United States Patent [19]
Walt et al.

[11] Patent Number: 5,244,813
[45] Date of Patent: Sep. 14, 1993

[54] FIBER OPTIC SENSOR, APPARATUS, AND METHODS FOR DETECTING AN ORGANIC ANALYTE IN A FLUID OR VAPOR SAMPLE

[75] Inventors: David R. Walt, Lexington, Mass.; Steven M. Bernard, Basel, Switzerland

[73] Assignee: Trustees of Tufts College, Medford, Mass.

[21] Appl. No.: 870,949

[22] Filed: Apr. 20, 1992

Related U.S. Application Data

[63] Continuation-in-part of Ser. No. 645,787, Jan. 25, 1991.

[51] Int. Cl.$^5$ .................. G01N 21/00; G01N 21/75; G01N 21/76
[52] U.S. Cl. .................. 436/172; 436/167; 385/12; 422/82.06; 422/82.07; 422/88; 422/86
[58] Field of Search .................. 128/634; 385/12; 422/82.06, 82.07, 82.08, 82.09, 86, 88; 436/91, 126, 127, 128, 129, 130, 139, 140, 141, 142, 167, 172

[56] References Cited

U.S. PATENT DOCUMENTS

| | | | |
|---|---|---|---|
| 4,842,783 | 6/1989 | Blaylock | 385/12 |
| 4,929,561 | 5/1990 | Hirshfeld | 422/82.06 |
| 4,994,396 | 2/1991 | Leftowitz et al. | 436/127 |
| 4,999,306 | 3/1991 | Yafuso et al. | 128/634 |
| 5,000,901 | 3/1991 | Iyer et al. | 128/634 |
| 5,096,671 | 3/1992 | Kane et al. | 128/634 |
| 5,152,287 | 10/1992 | Kane | 128/634 |

*Primary Examiner*—Robert J. Warden
*Assistant Examiner*—T. A. Trembley
*Attorney, Agent, or Firm*—David Prashker

[57] ABSTRACT

The present invention provides fiber optic sensors, apparatus, methods of optical detection, and methods of sensor manufacture for detection of organic analytes having a fixed polarity. The sensor requires an optical fiber strand; an immobilized polarity-sensitive dye; and an immobilized polymeric material which not only contains the polarity-sensitive dye but also absorbs and partitions the organic analyte of interest.

11 Claims, 11 Drawing Sheets

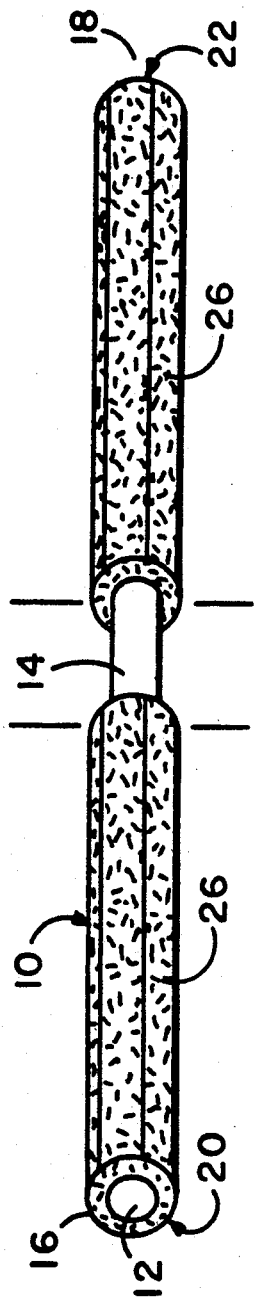
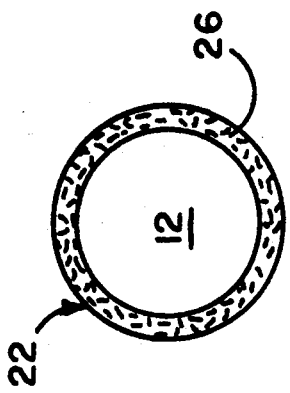
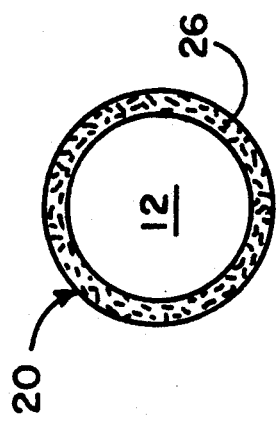
FIG. 1
FIG. 2B
FIG. 2A

FIBER OPTIC SENSOR, APPARATUS, AND METHODS FOR DETECTING AN ORGANIC ANALYTE IN A FLUID OR VAPOR SAMPLE

CROSS-REFERENCES

This application is a continuation-in-part of application Ser. No. 645,787 filed Jan. 25, 1991, now pending.

RESEARCH SUPPORT

The research for the present invention was supported by a grant from the Northeast Hazardous Substances Research Center, an Environmental Protection Agency Research Center for Federal Regions 1 and 2, through the Tufts Center for Environmental Management.

FIELD OF THE INVENTION

The present invention is concerned with optical sensors and optical sensing apparatus utilizing colorimetric or fluorometric techniques as qualitative and quantitative detection systems; and is particularly directed to fiber optic sensors utilizing polarity sensitive solvachromic dyes and polymeric materials capable of absorbing and partitioning organic analytes for optical determinations.

BACKGROUND OF THE INVENTION

The science and instrumentation of spectroscopy as developed over the last century has become increasingly expanded and specialized as the various methods and applications of analysis came into existence. Today, spectroscopy has been divided into individual and distinctly different methods and instrumentation systems for: ultraviolet and visible spectrophotometry; fluorescence and phosphorescence spectrometry; atomic emission spectroscopy; infrared spectrophotometry; raman spectroscopy; nuclear magnetic resonance spectroscopy; electron spin resonance spectroscopy; refractometry and interferometry; and various others. Of these, the optical sensors and optical sensing detection systems utilizing the ultraviolet and visible absorption methods and the fluorescence and phosphorescence excitation and emission systems are perhaps the best known and commonly utilized.

In particular, the use of optical fibers and optical fiber strands in combination with light energy absorbing dyes for medical, environmental, and chemical analytical determinations has undergone rapid development especially within the last decade. The use of optical fibers for such purposes and techniques generally is described by the following publications: Milanovich et al., "Novel Optical Fiber Techniques for Medical Application," Proceedings of the SPIE 28th Annual International Technical Symposium on Optics and Electro-Optics, Volume 494, 1980; Seitz, W. R., "Chemical Sensors Based on Immobilized Indicators and Fiber Optics," in *C.R.C. Critical Reviews in Analytical Chemistry*, Vol. 19, 1988, pp 135–173; Wolfbeis, O. S., "Fiber Optical Fluorosensors in Analytical Chemistry," in *Molecular Luminescence Spectroscopy, Methods and Applications* (S. G. Schulman, editor), Wiley & Sons, New York (1988); Angel, S. M., *Spectroscopy* 2(4):38 (1987); Walt et al., "Chemical Sensors and Microinstrumentation," *ACS Symposium Series*, volume 403, 1989, p 252; and Wolfbeis, CRC Press, 1991.

The optical fiber strands employed for analytical determinations typically are glass or plastic extended rods having a small cross-sectional diameter. When light energy is projected into one end of the fiber strand (conventionally termed the "proximal end"), the angles at which the various light energy rays strike the surface are greater than the critical angle; and such rays are "piped" through the strand's length by successive internal reflections and eventually exit from the opposite end of the strand (conventionally termed the "distal end"). Typically, bundles of these strands are used collectively as optical fibers in a variety of different applications.

For making an optical fiber into a sensor, one or more light energy absorbing dyes are attached to the distal end of the optical fiber. The sensor can then be used for both in-vitro and/or in-vivo applications. As used herein, light energy is photoenergy and is defined as electromagnetic radiation of any wavelength. Accordingly, the terms "light energy" and "photoenergy" include infrared, visible, and ultraviolet wavelengths conventionally employed in most optical instruments and apparatus; the term also includes the other spectral regions of x-ray and microwave wavelengths (although these are generally not used in conjunction with optical fibers).

Typically, light from an appropriate energy source is used to illuminate what is chosen to be the proximal end of an optical fiber or a fiber bundle. The light propagates along the length of the optical fiber; and a portion of this propagated light energy exits the distal end of the optical fiber and is absorbed by one or more light energy absorbing dyes. As conventionally known, the light energy absorbing dye may or may not be immobilized; may or may not be directly attached to the optical fiber itself; may or may not be suspended in a fluid sample containing one or more analytes of interest to be detected; and may or may not be retainable for subsequent use in a second optical determination.

Once the light energy has been absorbed by the dye, some light energy of varying wavelength and intensity typically returns through the distal end of the optical fiber and is then conveyed through either the same fiber or a collection fiber or fibers to a detection system where the emerging light energy is observed and measured. The interactions between the incoming light energy conveyed by the optical fiber and the properties of the light absorbing dye—both in the presence of a fluid sample containing one or more analytes of interest and in the absence of any analytes whatsoever—provide an optical basis for both qualitative and quantitative spectral determinations. Merely illustrating the use of some presently known optical fiber sensors in a variety of different conditions, apparatus, dyes, and applications are U.S. Pat. Nos. 4,822,746; 4,144,452; 4,495,293; and Re. 31,879.

Moreover, in view of the microcircuitry and enhanced television technology presently available, a variety of light image processing and analytical system have now come into existence in order to enhance, analyze, and mathematically process the light energies introduced to and emerging from the absorbing dyes in such optical analytical techniques. Typically, these systems provide components for image capture; data acquisition; data processing and analysis; and visual presentation to the user. Commercially available systems include the QX-7 image processing and analysis system sold by Quantex, Inc. (Sunnydale, Calif.); and the IM Spectrofluorescence imaging system offered by SPEX Industries, Inc. (Edison, N.J.). Each of these systems may be combined with microscopes, cameras, and/or television monitors for automatic processing of all light energy determinations.

Of the many different classes of light absorbing dyes which may be employed with single optical fiber strands and with bundles of optical fibers for different analytical purposes are those compositions which emit light energy after first absorbing energy and are termed "fluorophores"; and those compositions which absorb light energy and internally convert the absorbed light energy into heat or kinetic energy rather than emit it as light and are termed "chromophores" or "absorbers". Fluorophores and fluorescent detection methods employing optical fibers are recognized as being markedly different and distinguishable from light energy absorbance and absorption spectroscopy.

Fluorescence is a physical phenomenon based upon the ability of some molecules to absorb light energy (photons) at specified wavelengths and then emit light energy of a longer wavelength and at a lower energy. Such emissions are called fluorescence if the emission is relatively long-lived, typically $10^{-11}$ to $10^{-7}$ seconds. Substances able to fluoresce share and display a number of common characteristics: they absorb light energy at one wavelength or frequency; reach an excited energy state; and subsequently emit light at another light frequency and energy level. The absorption and fluorescence emission spectra are thus individual for each fluorophore; and are often graphically represented as two separate curves which are slightly overlapping.

All fluorophores demonstrate the Stokes' shift—that is, the emitted light is always at a longer wavelength (and at a lower energy level) relative to the wavelength (and energy level) of the exciting light absorbed by the substance. Moreover, the same fluorescence emission spectrum is generally observed irrespective of the wavelength of the exciting light and, accordingly, the wavelength and energy of the exciting light may be varied within limits; but the light emitted by the fluorophore will always provide the same emission spectrum as emerging light. Finally, fluorescence may be measured as the quantum yield of light emitted. The fluorescence quantum yield is the ratio of the number of photons emitted in comparison to the number of photons initially absorbed by the fluorophore. For more detailed information regarding each of these characteristics, the following references are recommended: Lakowicz, J. R., *Principles of Fluorescence Spectroscopy*, Plenum Press, New York, 1983; Freifelder, D., Physical Biochemistry, second edition, W. H. Freeman and Company, New York, 1982; "Molecular Luminescence Spectroscopy Methods and Applications: Part I" (S. G. Schulman, editor) in *Chemical Analysis*, vol. 77, Wiley & Sons, Inc., 1985; *The Theory of Luminescence*, Stepanov and Gribkovskii, Iliffe Books, Ltd., London, 1968.

In comparison, substances which absorb light energy and do not fluoresce usually convert the light energy into heat or kinetic energy. The ability to internally convert the absorbed light energy identifies the dye as a "chromophore." Dyes which absorb light energy as chromophores do so at individual wavelengths of energy and are characterized by a distinctive molar absorption coefficient for light energy at that wavelength. Chemical analyses employing fiber optic strands and absorption spectroscopy using visible and ultraviolet light wavelengths in combination with the absorption coefficient allow for the determination of concentration for specific analytes of interest by spectral measurement. The most common use of absorbance measurement via optical fibers is to determine concentration which is calculated in accordance with Beers' law; accordingly, at a single absorbance wavelength, the greater the quantity of the composition which absorbs light energy at a given photowavelength, the greater the optical density for the sample. In this way, the total quantity of light absorbed directly correlates with the quantity of the composition in the sample.

Many of the recent improvements employing optical fiber sensors in both qualitative and quantitative analytical determinations concern the desirability of depositing and/or immobilizing various light absorbing dyes at the distal end of the optical fiber using a given technique or apparatus. In this manner, a variety of different optical fiber chemical sensors and methods have been reported for specific analytical determinations and applications such as pH measurement, oxygen detection, and carbon dioxide analyses. These developments are represented and exemplified by the following publications: Freeman et al., *Anal. Chem.* 53:98 (1983); Lippitsch et al., *Anal. Chem. Acta.* 205:1, (1988); Wolfbeis et al., *Anal. Chem.* 60:2028 (1988); Jordan et al., *Anal. Chem.* 59:437 (1987); Lubbers et al., *Sens. Actuators*, 1983; Munkholm et al., *Talanta* 35:109 (1988); Munkholm et al., *Anal. Chem.* 58:1427 (1986); Seitz, W. R., *Anal. Chem.* 56:116A-34A (1984); Peterson et al., *Anal. Chem.* 52:864 (1980); Saari et al., *Anal. Chem.* 54:821 (1982); Saari et al., *Anal. Chem.* 55:667 (1983); Zhujun et al., *Anal. Chem. Acta.* 160:47 (1984); and Schwab et al., *Anal. Chem.* 56:2199 (1984).

Concurrent with developments in fiber optic technology have been the dramatic and devastating changes in our environment. Over the last several decades there has been increasing awareness and concern over organic contamination from hazardous waste sites and underground storage tanks. This contamination threatens the quality of groundwater at aquifers, thereby polluting the only drinking water source in many communities. These concerns have generated a massive effort of sampling and analysis at an ever-increasing number of monitoring wells. Existing monitoring technology [as described in Koehn, J. W. and G. H. Stanko, Jr., *Environ. Sci. Technol.* 22:1262-1263 (1988)] relies typically on expensive, labor-intensive, discrete sample methods that introduce uncertainties in the sampling and handling procedures. Often there is a long delay between sample collection and communication of results caused by the inability of conventional methods to provide in situ real-time monitoring. Moreover, extensive documentation is required due to chain-of-custody concerns. The application and generation of a low-cost reliable monitoring system employing fiber optic sensors and fiberoptic detection apparatus would reduce the need for frequent samples and provide timely continuous information of water quality.

SUMMARY OF THE INVENTION

The present invention provides optical fiber articles, apparatus, and methods able to be employed in the field for low cost and reliable systems for monitoring the environment in a timely and continuous manner. One aspect of the present invention thus provides a fiber optic sensor for detecting an organic analyte of interest in a fluid sample, said fiber optic sensor comprising:

an optical fiber strand able to convey light energy of a predetermined wavelength, said optical fiber strand having a proximal end, a distal end, and a strand length;

at least one polarity-sensitive dye immobilized at the distal end of said optical fiber strand, said polarity-sensitive dye being able to absorb light energy of a predetermined wavelength; and at least one polymeric material immobilized at the distal end of said optical fiber strand such that said immobilized polarity-sensitive dye is contained within said polymeric material, through which at least a portion of such organic analyte as is presented by the fluid sample becomes absorbed and partitioned by said immobilized polymeric material and a measurable change in the spectral properties of contained polarity-sensitive dye is produced.

A second aspect of the present invention provides a fiber optic sensor apparatus for detecting an organic analyte in a fluid sample, said apparatus comprising:

at least one fiber optic sensor comprised of an optical fiber strand able to convey light energy of a predetermined wavelength, said optical fiber strand having a proximal end, a distal end, and a strand length;

at least one polarity-sensitive dye immobilized at the distal end of said optical fiber strand, said polarity-sensitive dye being able to absorb light energy of a predetermined wavelength; and at least one polymeric material immobilized at the distal end of said optical fiber strand such that said immobilized polarity-sensitive dye is contained within said polymeric material, through which at least a portion of such organic analyte as is presented by the fluid sample becomes absorbed and partitioned by said immobilized polymeric material and a measurable change in the spectral properties of said contained polarity-sensitive dye is produced;

means for introducing light energy of a predetermined wavelength to the proximal end of said fiber optic sensor; and means for detecting light energy emitted by said contained polarity-sensitive dye.

Moreover, a third aspect of the present invention provides a method for detecting an organic analyte of interest in a fluid sample, said method comprising the steps of:

contacting the fluid sample comprising the organic analyte of interest with a fiber optic sensor comprised of an optical fiber strand able to convey light energy of a determinable wavelength, said optical fiber strand having a proximal end, a distal end, and a strand length, at least one polarity-sensitive dye, immobilized at the distal end of said optical fiber strand, said polarity-sensitive dye being able to absorb light energy of a determinable wavelength, and at least one polymeric material immobilized at the distal end of said optical fiber strand such that said immobilized polarity-sensitive dye is contained within said polymeric material, through which at least a portion of such organic analyte as is presented by the fluid sample becomes absorbed and partitioned by said immobilized polymeric material and a measurable change in the spectral properties of said contained polarity-sensitive dye is produced;

introducing light energy of a predetermined wavelength to the proximal end of said fiber optic strand whereby said light energy is conveyed to said distal end of said strand and said contained polarity-sensitive dye absorbs at least a portion of said light energy; and detecting light energy emittedd by said contained polarity-sensitive dye at said distal end of said fiber optic sensor, said detected light energy being a measure of the organic analyte in the fluid sample.

Yet a fourth aspect of the present invention provides a method for making a fiber optic sensor able to detect an organic analyte of interest in a fluid sample, said method comprising the steps of:

obtaining an optical fiber strand able to convey light energy of a predetermined wavelength, said optical fiber strand with at least one polymerizable material to form a reaction mixture; having a proximal end, a distal end, and a strand length;

admixing at least one polarity-sensitive dye able to absorb exciting light energy of a predetermined wavelength with at least one polymerizable material to form a reaction mixture; and polymerizing said reaction mixture at the distal end of said optical fiber strand such that said polarity-sensitive dye is contained within said immobilized polymeric material, through which at least a portion of such organic analyte as is presented by the fluid sample becomes absorbed and partitioned by said immobilized polymeric material and a measurable change in the spectral properties of said contained polarity-sensitive dye is produced.

BRIEF DESCRIPTION OF THE FIGURES

The present invention may be more easily and completely understood when taken in conjunction with the accompanying drawing, in which:

FIG. 1 is a perspective view of a single, optical fiber strand;

FIGS. 2A and 2B are overhead views of the proximal and distal ends of the single optical fiber strand of FIG. 1;

DETAILED DESCRIPTION OF THE INVENTION

Figure 3B:
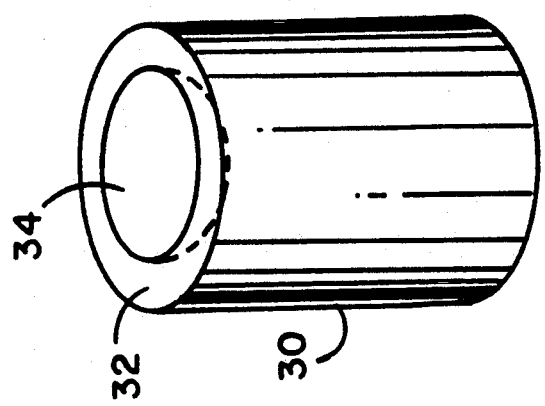
FIGS. 3A and 3B are perspective views of alternative embodiments for the distal end of an optical fiber strand.

The present invention is a marked improvement in fiber optic sensors, apparatus, and methods for performing qualitative and quantitative optical measurements and determinations of organic analytes. The physical construction of this singular and unique fiber optic sensor and the manner of its manufacture are the most critical and demanding aspects of the subject matter as a whole which is the present invention. The apparatus, the methods for making optical determinations, and the systems of qualitative and quantitative detection subsequently described are based and rely upon the existence and use of the properly constructed fiber optic sensors as the essential article.

Although the unique fiber optic sensor and the alternative constructions and methods employing this sensor as described hereinafter may bear a superficial similarity to conventionally known optical fiber strands, sensors, and fluorometric or colorimetric optical systems for making analytical determinations, it will be recognized and appreciated that the subject matter as a whole which is the present invention provides multiple benefits and major advantages not previously known or available heretofore. Among these benefits and advantages are the following:

1. A fully constructed fiber optical sensor comprising an individually clad, optical fiber strand which has at least one immobilized polarity-sensitive solvachromic dye and at least one immobilized polymeric material at the distal end. The immobilized polarity-sensitive dye is able to absorb light energy at a determinable wavelength; and the immobilized polymeric material encloses and encompasses the immobilized polarity-sensitive dye such that at least a portion of the organic analyte becomes absorbed and partitioned by the immobilized polymeric material concomitant with making reactive contact with the immobilized polarity-sensitive dye itself. This unique mode of construction and organization permits the use of many different dyes to measure a variety of different organic analytes, the critical requirement for the immobilized dye being only that it be polarity-sensitive. Similarly, the use of an immobilized polymeric material whose primary function is to absorb and partition at least a portion of such organic analyte of interest as is present is a distinctive and requisite feature of the fiber optic sensor. This sensor construction is uniquely simple and reproducible as a chemical detector; and allows reliable, accurate, and precise determinations of various organic analytes which were not conveniently detectable before.

2. The present fiber optic sensor, apparatus, and methodology for detection allows for several different mechanisms of interaction—a situation which is completely different and divergent from those systems conventionally employed for detection of organic analytes. The critical and essential interaction (regardless of mechanism) occurs between the immobilized polarity-sensitive dye, the sensor microenvironment provided by the immobilized polymeric material, and the presence or absence of the organic analyte of interest. Before the organic analyte is introduced, the spectral properties and the degree to which the immobilized polarity-sensitive dye absorbs and releases light energy of a given wavelength is directly influenced by the surrounding immobilized polymeric material in which the dye is contained and dispersed. However, after the organic analyte of interest is introduced to the sensor and the polymeric material has absorbed and at least partially partitioned the organic analyte, the spectral properties and the degree to which the immobilized polarity-sensitive dye absorbs and releases light energy of a given wavelength is now influenced by a combined resulting effect provided by the surrounding polymeric material as altered and modified by the absorbed and partitioned organic analyte then present within the local polymeric microenvironment. Thus, it is the merged result of the polymeric material's individual properties in combination with the additional influences exerted by the absorbed and partitioned organic analyte in-situ within the polymeric material that causes the polarity-sensitive dye contained within the local microenvironment to alter its light energy absorbing and releasing properties in measurable degree. Consequently, it is the change in the microenvironment generated by the presence of the organic analyte within the polymeric material that causes meaningful and discernable difference in spectral properties of the immobilized dye; and thus the presence or absence of the organic analyte of interest can be detected in a sensitive and reproducible manner by the change in light energy absorbing and releasing properties for the immobilized dye. This form of interaction and spectral change is truly unique in the art.

3. The fiber optic sensor, apparatus, and methods for detection may be employed with organic analytes which are volatile or non-volatile. The invention is of particular value for accurate determination of organic analytes such as hydrocarbons, including those principally present in petroleum products. The sensor is most sensitive to lower molecular weight hydrocarbons because these have high rates of diffusion within the polymeric material and thus allow a rapid rate of absorption and partition. This consequently permits such lower molecular weight hydrocarbons to come into contact with the immobilized polarity-sensitive dye in an unusually fast time period and thus provides the sensor with a rapid response time. Such hydrocarbons also have relatively high solubilities within the polymeric material which also provides highly sensitive optical determinations when using the fiber optic sensor.

4. The sensor, apparatus, and methods of detection permit determinations and measurement of organic analytes in the gaseous or vaporized state as well as in the liquid state. The present fiber optic sensor is a major improvement over laboratory based analytical methods such as gas chromatography in that the present sensor may be used practically in the field or environment generally, thus avoiding the major delays currently associated with sampling and transit time presently required; and eliminates sources of additional error due to sample handling.

5. The present invention is intended to be operated in-situ, dwelling at the point of analysis. This eliminates the long recognized problems in obtaining a representative sample ex-situ for analysis. While some of the present available methods may also be used in the field, each of them requires actually drawing a sample from the source and then analyzing the limited sample quantity. In contrast, the present invention allows a fiber optic sensor to be itself inserted into the source such as a well containing potable or contaminated water, a municipal reservoir, contaminated soil, or the vapor space surrounding under- or above-ground storage tanks. Thus, the present invention does not require removal of sample for analysis. To the contrary, the results are the direct evaluation and determination of the fluid composition as it occurs over time in the environment and at the naturally occurring source of the fluid.

6. The present fiber optic sensor, apparatus, and method of optical determinations provide practical results in a matter of minutes or seconds and thus provide immediate data. This real time analysis and determination capability is presently unavailable by conventionally known apparatus and is a necessity in practical terms for monitoring a process or for following the effects of environmental hazards or controls. In addition, the fiber optic sensor permits continuous monitoring if desired, or monitoring and direct analysis at present time intervals or within a scheduled program of determinations over time.

7. The present fiber optic sensor, apparatus, and methodology provide a more sensitive analysis and determination than is presently possible by other conventionally known in-situ devices such as metal-oxide sensors which typically detect only several hundred parts per million vapor volume concentration. The present invention achieves at least another order of magnitude in sensitivity generally; and with respect to known chemical sensors for detection of hydrocarbons, is unusually sensitive because a discernible response signal (with respect to background noise) is generated at markedly lower organic analyte concentrations.

8. The present fiber optic sensor, apparatus, and method for detection are completely automatic and require no human intervention from the time of placing the sensor in the desired location to the time of recording of the signal representing the raw data itself. This capability and advantage is of major importance because so much of the present and future needs for analytical determinations is for remote environment monitoring such as at storage tank sites, in wells, and within and along pipelines. The present invention also permits repeated use as a field screening device and technique which would detect the presence of organic analytes which are major pollutants; and then would trigger additional sampling automatically for a more comprehensive analysis at multiple sites. This automatic sensing and monitoring can be an essentially continuous operation if desired because the cost of continuous operation does not markedly increase with a large increase in the number of actual analyses. Alternatively, the monitoring may be performed on a regular or irregular time schedule at one or more locations, concurrently or in series.

Since the present invention is definable alternatively in multiple formats as a fiber optic sensor, an apparatus, a method for detection, and a method of manufacture; and may be employed in a variety of divergent purposes and applications to detect a large and diverse range of organic analytes of interest, the subject matter as a whole which is the present invention will be presently described in multiple textual sections individually and collectively in order that the prospective user may more quickly recognize and appreciate their major differences and distinctions in comparison to the fiber optic sensors, apparatus, and systems conventionally known today.

I. The Construction and Organization of the Fiber Optic Sensor

The singular fiber optic sensor is comprised of three essential components: an optical fiber strand; at least one polarity-sensitive or solvachromic dye immobilized at the distal end of the optical fiber strand; and at least one polymeric material immobilized at the distal end of the optical fiber strand such that the immobilized polarity-sensitive solvachromic dye is contained within (i.e., dispersed in and enclosed by) the polymeric material. Each component will be individually described in detail.

A. The Optical Fiber Strand

A preferred optical fiber strand is illustrated by FIGS. 1 and 2A and 2B. As seen therein, an individual optical fiber strand 10 is comprised of a single optical fiber 12 having a cylindrical shaft 14 and two fiber ends 16, 18, each of which provides a substantially planar end surface. The intended distal surface 20 at the fiber end 16 is illustrated by FIG. 2A while the intended proximal surface 22 at the fiber end 18 is illustrated within FIG. 2B. It will be recognized and appreciated that the terms "proximal" and "distal" are relative and interchangeable until the strand is ultimately positioned in an apparatus. The optical fiber 12 is composed typically of glass or plastic and is a flexible entity able to convey light energy introduced at either of its ends 16,18. Such optical fibers 12 are conventionally known and commercially available. Alternatively, the user may himself prepare optical fibers in accordance with the conventional practices and techniques reported by the scientific and industrial literature. For these reasons, the optical fiber 12 is deemed to be conventionally known and available as such.

It will be appreciated that FIGS. 1-2 are illustrations in which the features have been purposely magnified and exaggerated beyond their normal scale in order to provide both clarity and visualization of extreme detail. Typically, the conventional optical fiber strand has a cross-section diameter of 10-1,000 micrometers and is routinely employed in lengths ranging between centimeters (in the laboratory) to kilometers (in field telecommunications). Moreover, although the optical fiber is illustrated via FIGS. 1-2 an extended cylinder having substantially circular proximal and distal end surfaces, there is no requirement or demand that this specific configuration be maintained. To the contrary, the optical fiber may be polygonal or asymmetrically shaped along its length; provide special patterns and shapes at the proximal and/or distal faces; and need not present an end surface which is substantially planar. Nevertheless, for best results, it is presently believed that the substantially cylindrical rod-like optical fiber strand having planar end surfaces is most desirable.

Each optical fiber strand 12 is desirably, but not necessarily, individually clad by cladding 26 axially along its length. This cladding 26 is composed of any material which has a lower refractive index and prevents the transmission of light energy photons from the optical fiber 12 to the external environment. The cladding material 26 may thus be composed of a variety of radically different chemical formulations including various glasses, silicones, plastics, cloths, platings, and shielding matter of diverse chemical composition and formulation. The manner in which the optical fiber 12 is clad is inconsequential and of no importance to the present invention. Those methods of deposition, extrusion, painting, and covering are scientifically and industrially available; and any of these known processes may be chosen to meet the requirements and convenience of the user. Moreover, the quantity of cladding employed need be only that minimal amount which effectively prevents light energy conveyed by the optical fiber 12 from escaping into the general surroundings. It will be recognized and appreciated therefore that the depth of cladding 26 as appears within FIGS. 1 and 2 respectively is greatly exaggerated and purposely thickened in order to show the general relationship; and is without scale or precise ratio between the cladding 26 and the optical fiber 12.

It will also be recognized that the configuration of the cladding 26 as appears within FIGS. 1 and 2 has been shaped as a round coating as a preferred embodiment only. Alternatively, it is often desirable that the cladding take shape in specific multi-sided and regular geometric forms such as a round, oval, circular, or even irregular shape. The illustrated configuration, however, is merely one embodiment of the cladding 26 as it extends co-axially along the length of the optical fiber strand 10. For purposes of added clarity also, FIG. 1 reveals the individual clad, optical fiber strand 12 in partial cross-section views to demonstrate the relationship between the optical fiber 12 and the cladding 26 which is coextensive along its length.

Figure 3A:
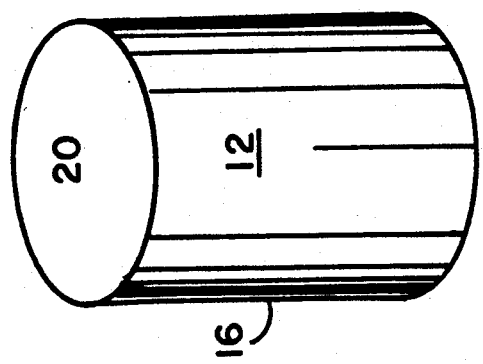

The user also has a variety of choices at his discretion regarding the configuration of the distal end 16 of the optical fiber strand 12 as is demonstrated by FIGS. 3A and 3B. As seen via FIG. 3A, the distal end 16 is substantially cylindrical in shape and desirably presents a surface 20 which is substantially planar and smooth. As an alternative in FIG. 3B, the distal end 30, while maintaining its substantially cylindrical shape, nevertheless provides a very different end surface for the optical fiber 12. The surface 32 includes a depression or well 34 which extends into the substance of the optical fiber 12 at a depth typically of several micrometers. Although the well 34 appears substantially circular within FIG. 3B, oval or irregularly configured depressions may also be employed as fits the needs or convenience of the user. Similarly, the void volume of the well 34 from its greatest depth to the surface 32 may also be considerably varied.

It will be recognized and appreciated as well that the range and variety of dimensional and configurational divergence for the strand end is limited only by the user's ability to subsequently dispose and immobilize a polarity-sensitive dye composition/formulation on the intended distal surface of the optical fiber 12. The alternative illustrated by FIG. 3B will increase the quantity of dye material deposited and also permit a greater surface area of dye for reactive contact on the surface for specific uses and assay applications. In some embodiments, the greatest possible surface area configurations of the distal end surface may be highly desirable; nevertheless, for most general assay purposes, both quantitative and qualitative, the intended distal surface illustrated within FIG. 3A as a substantially planar and smooth surface is deemed to be suitable and desirable. For general construction of the optic fiber sensor and for most purposes and applications of the improved optical detecting system and procedures described hereinafter, it is desirable to employ the individually clad, fiber optical strand illustrated by FIGS. 1, 2A, and 2B.

B. The Polarity-Sensitive or Solvachromic Dye

The second critical requirement and feature of the present fiber optic sensor is the presence of at least one polarity-sensitive or solvachromic dye immobilized at the intended distal end of the optical fiber strand. Solvachromic dyes, regardless of specific composition and formulation, are identified and defined in operational terms as a light energy absorbing substance whose absorption and/or emission spectra are sensitive to and altered by the polarity of their surrounding environment—including gaseous, liquid, and/or solid molecules and ions which are temporarily or permanently present in the immediately adjacent spatial volume. The term "solvachromic" is derived from the recognized and long established characteristics of many fluorophores whose fluorescence emission spectra are sensitive to the polarity of the solvents in which they are employed or found. For example, if the emission spectrum of a fluorophore such as ANS (1-anilino-8-naphthalenesulfonyl acid) is examined in different solvents of varying polarity, one finds that the emission spectrum shifts to shorter wavelengths (blue shifts) as the solvent polarity is decreased. Conversely, increasing solvent polarity generally results in shifts of the emission spectrum of the fluorophore to longer wavelengths (red shifts). Red shifts are often, but not always, accompanied by a decrease in the quantum yield or total of photons emitted for the fluorophore being evaluated. This phenomenon, the change in emission spectrum of many fluorophores with respect to different solvents of varying polarity, is well described by the following publications: Joseph R. Lakowicz, *Principles of Fluorescence Spectroscopy*, Chapter 7, Plenum Press, New York, 1983, pp 187-255; Mataga et al., *Bull. Chem. Soc. Jpn.* 29:465-470 (1956); Bakhishiev, N.G., *Opt. Spectrosc.* 10:379-384 (1961), and *Opt. Spectrosc.* 12:309-313 (1962), and *Opt. Spectrosc.* 13:24-29(1962); MacGregor, R.B. and G. Weber, *Proc. N.Y. Acad. Sci.* 366:140-154 (1981).

While the best known examples of solvachromic dyes are fluorophores, the membership of this class as a whole includes both absorbers or chromophores as well as fluorescent molecules. The essential property common to each and every member of this class of dyes is that the chosen dye substance change its spectral properties when exposed to different solvents of varying polarity. For fluorophores, this spectral change can include either an emission intensity charge or a change in the wavelength of the emitted fluorescent light. For an absorber or chromophore dye, the intensity of color may change or the absorption spectrum of the dye may shift either toward the red or the blue end of the spectrum. To determine whether a chosen dye composition is a member of the class defined as a solvachromic dye, the test is solely an empirical one. When the dye is exposed to different organic solvents of varying polarity, the dye changes its color which is empirically observed as a spectral change. Thus, an absorber dye demonstrates a spectral change through its color, either by altering the intensity of the color or by the observation of an actual color change. Alternatively, a fluorescent dye demonstrates its sensitivity to different solvents of varying polarity through changes in either its absorbing exciting light; or by a change in wavelength of the emitted light; or by a change in the intensity of the emitted light.

By this operational definition and the empirical test method through which any person of ordinary skill in this art may identify a chosen dye substance as being a solvachromic dye, it will be recognized and appreciated that the terms "solvachromic" and "polarity-sensitive" are directly related and often interchangeable. The meaning of each of these terms, however, is not exactly alike. To the contrary, the term "polarity-sensitive dye" defines and identifies a dye formulation which is not only sensitive to different solvents of varying polarity, but also to any other organic entity, molecule, or substance which has a discernable-that is, a demonstrable or determinable-polarity. Thus, organic compositions, compounds, and formulations of varying polarity which are not solvents as such are clearly encompassed and included by this term in addition to those compositions which are classically defined as "organic solvents." Thus, organic solvents constitute merely one group or family within the membership as a whole for the class of organic analytes having a discernable polarity. In this manner, while it is most convenient to test and evaluate a chosen dye using a plurality of solvents of varying polarity to empirically demonstrate that the chosen dye is spectrally influenced and altered by the polarity of the surrounding environment, any other kind or type or organic molecule may also be employed to demonstrate the spectral sensitivity of the chosen dye-albeit under less convenient and/or more rigorous test conditions.

To demonstrate the range and diversity of the membership comprising the class as a whole which constitutes polarity-sensitive or solvachromic dyes, a non-exhaustive listing of representative examples is provided hereinafter by Tables 1 and 2 respectively. Table 1 provides a representative list of polarity-sensitive fluorophores. Correspondingly, Table 2 provides a range of illustrative examples which are polarity-sensitive absorber or chromophoric dyes.

TABLE 1

POLARITY-SENSITIVE FLUOROPHORES

Phospholipid Fluorophores
N-(7-nitrobenz-2-oxa-1,3-diazol-4-yl)dipalmittcyl-L-a-phosphatidylethanolamine (NBD-PE)
N-(5-fluoresceinthiocarbamoyl)dipalmitoyl-L-a-phosphatidylethanolamine triethylammonium salt (fluorescein-PE)
N-(6-tetramethylrhodaminethiocarbamoyl)dipalmitoyl-L-a-phosphatidylethanolamine triethylammonium salt (TRITC DPPE)
N-(Lissamine rhodamine B sulfonyl)dipalmitoyl-L-a-phosphatidylethanolamine triethylammonium salt (rhodamine DPPE)
N-(Texas Red sulfonyl)diolsoyl-L-a-phosphatidylethanolamine triethylammonium salt
N-(Texas Red sulfonyl)dipalmitoyl-L-a-phosphatidylethanolamine triethylammonium salt (Texas Red DPPE)
3-palmitoyl-2-(1-pyrenedecanoyl)-L-a-phosphatidylcholine (10-py-PC)
N-(5-dimethylaminonaphthalene-1-sulfonyl)dipalmitoyl-L-a-phosphatidylethanolamine triethylammonium salt
N-(1-pyrenesulfonyl)dipalmitoyl-L-a-phosphatidylethanolamine triethylammonium salt
N-(6-(5-dimethylaminonaphthalene-1-sulfonyl)amino)-hexanoyldipalmitoyl-L-a-phosphatidylethanolamine triethylammonium salt
N-(biotinoyl)dipalmitoyl-L-a-phosphatidylethanolamine triethylammonium salt Anionic Fluorophores
cis-parinaric acid
trans-parinaric acid
p-((6-phenyl)-1,3,5-hexatrienyl)benzoic acid (DPH carboxylic acid)
3-(p-(6-phenyl)-1,3,5-hexatrienyl)phenylpropionic acid (DPH propionic acid)
1-pyrenecarboxylic acid
1-pyrenebutanoic acid (pyrenebutyric acid)
1-pyreneonanoic acid
1-pyrenedecanoic acid
1-pyrenedodecanoic acid
1-pyrenehexadecanoic acid
11-((1-pyrenesulfonyl)amino)undecanoic acid
2-(9-anthroyloxy)palmitic acid (2-AP)
2-(9-anthroyloxy)stearic acid (2-AS)
3-(9-anthroyloxy)stearic acid (3-AS)
6-(9-anthroyloxy)stearic acid (6-AS)
7-(9-anthroyloxy)stearic acid (7-AS)
9-(9-anthroyloxy)stearic acid (9-AS)
10-(9-anthroyloxy)stearic acid (10-AS)
11-(9-anthroyloxy)undecanoic acid (11-AU)
12-(9-anthroyloxy)stearic acid (12-AS)
12-(9-anthroyloxy)oleic acid (12-AO)
16-(9-anthroyloxy)palmitic acid (16-AP)
9-anthracenepropionic acid
9-anthracenedodecanoic acid
1-perylenedodecanoic acid
6-(N-(7-nitrobenz-2-oxa-1,3-diazol-4-yl)amino)haxanoic acid (NBD hexanoic acid)
12-(N-methyl)-N-((7nitrobenz-2-oxa-1,3-diazol-4-yl)amino)dodecanoic acid
12-(N-methyl-N-((7-nitrobenz-2-oxa-1,3-diazol-4-yl)amino)octadecanoic acid
12-(N-(7-nitrobenz-2-oxa-1,3-diazol-4-yl)amino)-dodecanoic acid
11-(9-carbazole)undecanoic acid (11-CU)
11-((5-dimethylaminonaphthalene-1-sulfonyl)amino)undecanoic acid
5-(N-dodecanoyl)aminofluorescein
5-(N-hexadecanoyl)aminofluorescein
5-(N-octadecanoyl)aminofluorescein
5-(N-hexadecanoyl)aminoeosin
1-anilinonaphthalene-8-sulfonic acid (1,8-ANS)
2-anilinonaphthalene-6-sulfonic acid (2,6-ANS)
2-(p-toluidinyl)naphthalene-6-sulfonic acid sodium salt (2,6-TNS)
2-(N-methylanilino)naphthalene-6-sulfonic acid sodium salt (2,6-MANS)
bis-ANS (1,1'-bi(4-anilino)naphthalene-5,5'-disulfonic acid, dipotassium salt)
1-pyrenesulfonic acid, sodium salt 2-(N-octadecyl)aminonaphthalene-6-sulfonic acid, sodium salt Cationic Fluorophores 1,1'-dihexadecyloxacarbocyanine, perchlorate (DiOC$_{16}$(3))
3,3'-dioctadecyloxacarboxyanine perchlorate ("DiO", DiOC$_{18}$(3))
1,1'-didodecyl-3,3,3',3'-tetramethylindocarbocyanine, perchlorate (DilC$_{12}$(3))
1,1'-dihexadecyl-3,3,3',3'-tetramethyolindocarbocyanine perchlorate (DilC$_{16}$(3))
1,1'-dioctadecyl-3,3,3',3'-tetramethylindocarbocyanine perchlorate (":Dil", DilC$_{18}$(3))
1,1'-didocosanyl-3,3,3',3'-tetramethylindocarbocyanine perchlorate (DilC$_{22}$(3))
1,1'-dioctadecyl-3,3,3',3'-tetramethylindodicarbocyanine perchlorate (DilC$_{18}$(5))
3,3'-dioctadecylthiacarbocyanine perchlorate (DiSC$_{18}$(3))
octadecyl rhodamine B, chloride salt (R 18)
rhodamine 6G, octadecyl ester, chloride
rhodamine 101, octadecyl ester, chloride
N-4-(4-didecylaminostyryl)-N-methylpyridinium iodide (4-di-10-ASP)
1-(4-trimethylammoniumphenyl)-6-phenyl-1,3,5-hexatriene, p-toluenesulfonate (TMA-DPH)
6-palmitoyl-2-(((2-(trimethyl)ammonium)ethyl)methyl)amino)naphthalene, chloride (PATMAN)
1-pyrenemethyltrimethylammonium iodide
1-pyrenebutyltrimethylammonium bromide
3-(-anthracene)propyl trimethylammonium bromide
acridine orange-10-dodecyl bromide (dodecyl acridine orange)
acridine orange-10nonyl bromide (nonyl acridine orange)

Neutral Fluorophores 1,6-diphenyl-1,3,5-hexatriene (DPH)
1-phenyl-6-((4-trifluoromethyl)phenyl)-1,3,5-hexatriene (CF-DPH)
palladium disodium alizarinmonosulfonate (Pd(QS)$_2$)
Nile Red or 9-diethylamino-5H-benzo[ ]phenoxazine-5-one
6-propionyl-2-dimethylaminonaphthalene (prodan)
6-dodecanoyl-2-dimethylaminonaphthalene (laurodan)
N-phenyl-11-naphthylamine
1,10-bis-(1-pyrene)decane
1,3-bis-(1-pyrene)propane
p-dimethylaminobenzylidenemalononitrile
N-(5-dimethylaminonaphthalene-1-sulfonyl)hexadecylamine
N-(5-dimethylaminonaphthalene-1-sulfonyl)dihexadecylamine
4-(N,N-dihexadecyl)amino-7-nitrobenz-2-oxa=1,3-diazole (NBD dihexadecylamine)
4-(N,N-dioctyl)amino-7-nitrobenz-2-oxa-1,3-diazole (NBD-dioctylamine)
4-(hexadecylamino)-7-nitrobenz-2-oxa-1,3-diazole (NBD hexadecylamine)
1-pyrenecarboxaldehyde
1-pyrenenonanol
7-dimethylamino-4-pentadecylcoumarin
cholesteryl anthracene-9-carboxylate
1-pyrenemethyl 36-hydroxyl-22,23-bisnor-5-cholenate (PMC)
1-pyrenemethyl 38-(cis-9-octadecenoyloxy)-22,23-bisnor-5-cholenate (PMC oleate)
25-(NBD-methylamino)-27-norcholesterol (NBD-MANC)
25-(NBD-methylamino)-27-norcholesteryl oleate (NBD-MANC oleate)
22-(N-(7-nitrobenz-2-oxa-1,3-diazol-4-yl)amino)-23,24-bisnor-5-cholen-38-ol
22-(N-(7-nitrobenz-2-oxa-1,3-diazol-4-yl)amino)-23,24-bisnor-5-cholen-38-yl linoleate
N-(3-sulfopropyl)-4-(p-didecylaminostyryl)pyridinium, inner salt (Dil0ASP-PS)
3-(N,N-dimethyl-N-(1-pyrenemethyl)ammonium)propanesulfonate, inner salt
4-(N,N-dimethyl-N-(1-pyrenemethyl)ammonium)butanesulfonate, inner salt
N-e-(5-dimethylaminonaphthalene-1-sulfonyl)-L-lysine (dansyl lysine)

TABLE 2

POLARITY-SENSITIVE CHROMOPHORES

Phospholipid Chromophores

2(3-diphenylhexatrienyl)propanoyl-3-palmitoyl-L-a-phosphatidyl choline (DPH-PC)
N-(6-(biotinoyl)amino hexanoyl) dipalmitoyl-L-a-phosphatidylethanolamine triethyl ammonium salt (biotin-X-DPPE)
N-((4-maleimidylmethyl)cyclohexane-1-carbonyl)dipalmitoyl-L-a-phosphatidylethanolamine triethylammonium salt (MMCC-DPPE)
N-((2-pyridyldithio)propionyl)dipalmitoyl-L-a-phosphatidylethanamine triethylammonium salt Anionic Chromophores 15-phenylpentadecanoic acid
5-(N-hexadecanoyl) amino fluorescein diacetate C. The Polymeric Material The third and final required component comprising the fiber optic sensor is the existence of at least one polymeric material immobilized at the distal end of the optical fiber strand such that the immobilized polarity-sensitive dye is contained within, that is—dispersed, enclosed, and/or encompassed by—this polymeric material. There are two characteristics and functions for the polymeric material as it relates to the sensor construction and performance. The first characteristic and function is the primary role of the polymeric material—capturing the organic analyte of interest to be detected. This capture function and capability is performed by absorbing and partitioning the organic analyte of interest within the substance and thickness of the polymeric material itself as it lies immobilized at the distal end of the optical fiber strand. The absorption and partition occurs between the vapor or liquid phase of the fluid sample and the polymeric material forming one component of the sensor construction. The partitioning of the organic analyte of interest may be similar within the fluid sample and in the polymeric material, that is the concentration of vapor in each of these two phases may be the same; or more likely, one of the two will be enriched in concentration of the organic analyte relative to the other. Under ideal circumstances, the polymeric material layer will serve to concentrate the organic analyte of interest via its superior solubility characteristics relative to the vapor or liquid phase. In preferred embodiments of the fiber optic sensor comprising the present invention, the polymeric material will concentrate the organic analyte, which in turn, increases the sensitivity and detection limit of the sensor as a unit.

The second function and characteristic of the polymeric material, which will not be present to a similar degree in all embodiments of the fiber optic sensor, is the spectral influence exerted by the polymeric material and its ability to alter or modify the spectral characteristics of the dye-independent and separate from the spectral influences and consequences caused by the organic analyte of interest. This second property and characteristic will often vary with the degree of polarity or the non-polarity of the polymeric material as individually chosen for use in constructing the specific embodiment. Polarity as such, however, is not the sole property or mechanism by which the dye's spectral properties are mediated or affected. Thus, the properties of the polymeric material containing the immobilized polarity-sensitive dye at the distal end of the optical fiber strand may or may not itself alone influence and alter the spectral characteristics of the immobilized solvachromic dye apart from and prior to introduction of an organic analyte in a fluid sample.

It will be noted, however, that the essential value and circumstance lies in the polymeric material interacting with the imobilized polarity-sensitive dye and thus providing a background or baseline of dye interaction and of dye spectral properties against which all other or subsequent optical determinations and measurements are made and compared. As a consequence of the polarity-sensitive dye being contained, dispersed, or otherwise immobilized within a particular polymeric material at one end of the optical fiber strand, a background or baseline set of spectral properties for the immobilized and contained dye is produced which are the result and consequence of only the interaction between the polymeric material and the polarity-sensitive dye. It is this baseline or background set of spectral characteristics against which all optical determinations and changes in spectral properties are subsequently made and measured for the detection of an organic analyte of interest.

Accordingly, when the fully constructed fiber optic sensor is then placed in contact with a fluid sample believed to contain one or more organic analytes having an inducible or fixed polarity, the organic analytes become captured, absorbed, and partitioned by the polymeric material and generates marked changes in the spectral properties of the immobilized polarity-sensitive dye in the sensor. Thus, directly as a result of the organic analyte's absorption and partitioning by the polymeric layer, the spectral light absorbing and light emitting characteristics of the immobilized dye become changed from its background or baseline standard provided by the effect of the polymeric material alone.

There is a large and diverse range of polymeric materials suitable for use when constructing the embodiments of the present fiber optic sensor. Many of these polymeric materials have been previously synthesized, characterized chemically, and are often commercially prepared. A representative, but non-exhaustive listing of polymeric materials suitable for use when constructing the present fiber optic sensors is presented by Table 3 below.

TABLE 3

POLYMERIC MATERIALS

Silicones and Silicon-Containing Polymers
Monomeric and oligomeric fluids (including silahydrocarbons)
Polydimethylsiloxanes-conventional fluids
Polydimethylsiloxanes, silanol and moisture cure prepolymers
Polydimethylsiloxanes, vinyl termination
Polydimethylsiloxanes, functional termination
Polydimethylsiloxanes, vinyl functional copolymers
Polydimethylsiloxanes, copolymers with functional groups
T-structure polymers with functionality
Organohydrosiloxane polymers and copolymers
Polymethylalkylsiloxanes
Fluoroalkylsiloxanes
Aromatic (phenyl containing) siloxanes
Aromatic polymers with functional groups
Aromatic substituted alkyl polysiloxanes
Silicone gums
Non-siloxane-siloxane copolymers
Polysilanes
Polysilazanes
Polyalkoxysiloxanes-polysilicatse (including sol-gel intermediates)
T-resins and ladder polymers
Silane-modified polymers (includingpolymeric coupling agents)
Other Polymers
polyethylene
polypropylene
polymethylmethacrylate
polystyrene
polyhydroxyethylmethacrylate
polyurethanes
polyvinylchloride
polyvinylidene chloride
fluorinated polyolefins
chlorofluoropolyolefins
polysubstituted siloxanes
Parafilm
\* copolymers of the above listed compounds D. Mechanism of Fiber Optic Sensor Operation and Function The sensors described herein are not controlled in operation or function by any particular mechanism of action. The spectral changes exhibited by the sensors which may be operative, will include: (1) polarity changes in the polymeric material generated by the organic analyte of interest which consequently can impart changes in the spectral properties of the dyes, as these dyes are sensitive to polarity; (2) concentration quenching wherein dyes can associate with one another and through this association diminish their light intensity, the degree of association being influenced by the presence or absence of the organic analyte; (3) changes orientational in nature, in which the polymer, in the presence of the organic analyte, orients the dye in a particular way which creates an environment for changed spectral properties; and (4) swelling in which the distance between dye molecules changes as a function of the volume change in the polymeric material caused by the introduction of the organic analyte.

II. Organic Analytes Having a Discernible Polarity

The analytes which may be optically detected and measured using the present invention individually and collectively share several characteristics and properties. The first and foremost property is that the organic analyte have a discernible polarity. The polarity includes polarity of bonds caused by two atoms joined by a covalent bond which share electrons unequally; and the polarity of molecules which occurs if the center of negative charge does not coincide with the center of positive charge within the molecular structure and thus constitutes a dipole.

The second commonly shared characteristic of the organic analytes having a discernible polarity is that they may in fact be in any physical state—that is in a gaseous, liquid, or even in a fluid-solid state. It is required that the organic analyte be able to migrate within or be carried by a fluid sample; to be absorbed and at least partially partitioned by the polymeric material immobilized at the tip of the sensor; and that the absorbed and partitioned analyte of interest present in the polymeric material layer meaningfully alter or modify the baseline set of spectral properties generated by the interaction of the immobilized solvachromic dye with the polymeric material which exists prior to introduction of the analyte of interest. Thus, so long as the organic analyte of interest has a discernible polarity and is in a mobile and transportable state wherein it can be conveyed, that organic analyte may be detected, identified, and determined optically by the present invention.

The majority of analytes suitable for detection by the present invention are expected primarily to be in the vapor or liquid physical states; and, moreover, that these be recognized conventionally as organic solvents which are well known and employed in research and industry. Nevertheless, such organic substances which appear as fluid solids in the field or in-situ are also suitable for detection and measurement using the present invention.

The third common property shared among the membership of organic analytes of discernible polarity is that they are primarily but not exclusively hydrocarbons. Such hydrocarbons are composed primarily of carbon and hydrogen atoms; but may also contain one or more heteroatoms selected from the group consisting of nitrogen, oxygen, sulfur, and halogen atoms. These hydrocarbons, with or without one or more heteroatoms, may be saturated or unsaturated; may take shape as linear, branched, ring, or polycyclic structures; and present formats which include aliphatic and aryl hydrocarbon structures or combinations of these. Moreover, it is intended and expected that the hydrocarbon molecule as a whole, exclusive of any heteroatoms which may optionally be present, will comprise from 1 to about 25 carbon atoms in total; and that within this range of carbon atoms, one or more degrees of saturation; linear, branched, and ring entities; and multiple structural formats will be present.

Since one of the major intended applications and advantageous uses of the present invention will be within the environmental area, with particular emphasis upon potable water sources and soil and water contamination from industrial sources, the fiber optic sensor and method of detection are particularly valuable for the detection of hydrocarbons principally present in petroleum products. These include petroleum aromatics, naphthalenes, paraffins, and olefins which are present within crude oil or derived as petroleum products.

The fiber optic sensor is particularly sensitive to and exceptionally able to detect lower molecular weight liquid hydrocarbons because such molecules have high solubility in and high diffusivities within the chosen polymeric material—thus permitting rapid absorption and partition by the polymeric material and a measurable change in the spectral properties of the immobilized polarity-sensitive dye within a reasonably fast response time. In comparison, for organic analytes which are normally gaseous (such as methane, ethane, and ethylene) the sensor is expected to have lower sensitivity in response because of the lower solubility of these analytes within the polymeric materials generally expected to be employed within the fully constructed sensor. High molecular weight liquid hydrocarbons would also be expected to take a somewhat longer time to be detected in comparison to low molecular weight hydrocarbons because of lower diffusivities in the polymeric material.

Regardless of the particular molecular weight of the entity which is to be detected using the present invention, any organic analyte which can penetrate and be captured by the polymeric material of the sensor (and thus be absorbed and partitioned during its migration) is suitable for detection using the present invention. The differences among the various hydrocarbons and other organic compounds would be only in the magnitude of their individual effects upon the polarity-sensitive dye; and the time required for the sensor to respond spectrally to the presence of the organic analytes within the fluid sample.

To demonstrate, a representative but preferred range of hydrocarbons suitable for detection by the present invention are in the listing of Table 4 provided below.

TABLE 4

HYDROCARBONS FROM PETROLEUM SOURCES SUITABLE FOR DETECTION

Aromatics such as benzene, toluene, the xylenes, ethyl benzene, naphthalene, anthracene, phenanthrene, plus their hydrocarbon derivatives;

Naphthenes (saturated cyclics) such as cyclohexane, tetralin, and their hydrocarbon derivatives;

Paraffins (branched and straight chain) such as propane; normal and isobutane; all paraffinic isomers of C5, C6, C7, C8, C9, and C10;

Olefins such as propylene; the butylenes; all olefinic isomers of C5, C6, C7, C8, C9, and C10;

Halogenated hydrocarbons comprising chlorine, bromine, fluorine, or iodine; and

Hydrocarbons of up to 25 carbon atoms containing one or more carbonyl groups (-CO) forming aldehydes and ketones.

III. Means for Immobilizing the Polarity-Sensitive Dye and the Polymeric Material The manufacture of the fiber optic sensor as described herein requires that the polarity-sensitive dye and the polymeric material each be deposited and immobilized at the intended distal end of at least one optical fiber strand. Not only must each of these components be immobilized at the tip of the optical fiber strand; but also it is required that the immobilized polymeric material enclose and encompass the entirety of the polarity-sensitive dye to achieve the intended construction organization. Thus, a highly desirable approach and method for manufacture purposefully combines the polarity-sensitive dye with monomers, or co-polymers, or prepolymers to form the polymer; and then polymerizes or cross-links the mixture in-situ directly at the intended distal end of the optical fiber strand. By this method, the polarity-sensitive dye is intimately intermixed and dispersed within the substance and thickness of the polymeric material and does not present any discrete format or layer as such.

The preferred method of deposition and immobilization is via a coating polymerization and employs an admixture of monomers and/or prepolymers with one or more pre-chosen polarity-sensitive dye as a formulation. Such admixture preparations typically comprise solutions of several monomers and/or prepolymers in admixture and a concentration of at least one polarity-sensitive dye. A representative listing of different monomer and prepolymer compositions suitable for preparing an admixture are given by Table 5. Such admixtures subsequently can be polymerized or solidified by solvent evaporation to form the desired polymer matrix. An illustrative listing of polarity-sensitive dyes ready for admixture and polymerization is given previously by Tables 1 and 2 above. It will be appreciated that conventionally known techniques of polymerization including thermal, free radical, and photopolymerization are known and available to the user.

TABLE 5

A. Monomers
  acrylamide
  N,N-methylene bis(acrylamide)
  hydroxyethylmethacrylate
  styrene
  vinyl acetate
  N-(3-aminopropyl)meth-acrylamide hydrochloride [Kodak, Inc.]
B. Comonomer With Dimethylsiloxane
  (acryloxypropyl) methyl (15-20%)
  (aminopropyl) methyl (3-5%)
  (methacryloxypropyl) methyl (2-3%)
C. T-Structure Polydimethylsiloxanes
  methacryloxypropyl (25-50%)
  vinyl (50-75%)
D. Waxes/Preformed Polymers
  paraffin
  polyvinyl alcohol It will be appreciated that the listings of Tables 1, 2, and 5 are merely exemplary of the many different compositions which can be usefully employed in admixture with one or more solvachromic dyes. In addition, the scientific and industrial literature provides many alternative monomer preparations and admixtures which are also suitable for use in making the present invention. Accordingly, all of these conventionally known monomer preparations are considered to be within the scope of the present invention.

IV. A Preferred Embodiment of the Fiber Optic Sensor

To demonstrate a most desirable method of making the unique fiber optic sensor comprising part of the present invention; and as a demonstration of the utility and effectiveness for making optical determinations using a fully constructed prepared embodiment of the fiber optic sensor, a detailed description of the components and manipulative steps for making a sensor able to measure volatile organic compounds in ground water and soil samples is presented. It will be expressly understood, however, that the detailed description which follows hereinafter is merely illustrative and representative of the many different kinds of sensors which can be made having one or more polarity-sensitive dyes and polymeric materials immobilized on one optical strand end surface.

Fiber-Optic Materials: The optical fiber strand used to construct the sensor was 600 μm in diameter, 5 m in length, having a numerical aperture of 0.37 and coated with a protective plastic jacket (Ensign-Bickford Optics Co., Avon, Conn.). The proximal end was coupled to a fluorometer by an Optimate Connector (AMP Inc., Harrisburg, Pa). The distal end was stripped, cleaved, polished, and then cleaned with concentrated sulfuric acid.

Surface Silanization: The distal tip of the fiber was soaked in 10% (v/v) octadecyltriethoxysilane (Petrarch Systems Inc., Bristol, Pa.) in dry acetone overnight to improve polymer adhesion. The fiber was rinsed with acetone and dried in an oven for 1 hour at 100° C.

Figure 4:
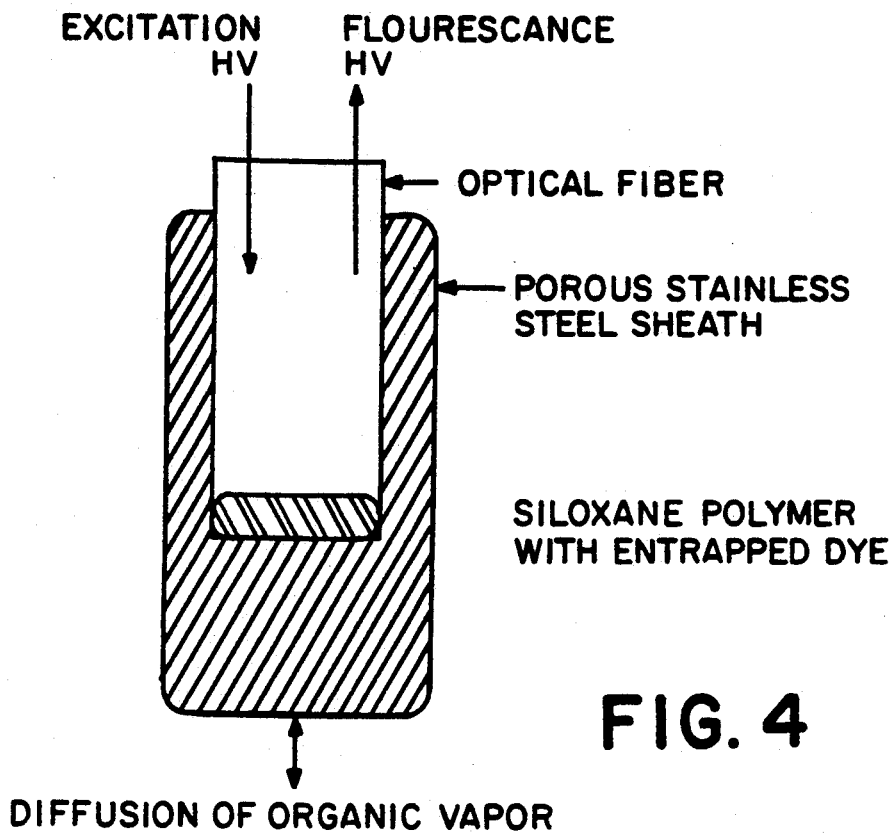
FIG. 4 is a cross-sectional view of the sensor configuration for an organic vapor sensor.

Sensor Construction: The sensor configuration and materials are shown in FIG. 4. The sensing layer was applied by solvent evaporation. The distal tip was dipped into a solution containing 0.314 mM Nile Red (Molecular Probes, Eugene, OR) and 10% (v/v) Dow Corning (Lansing, Mich.) dispersion coating compound in toluene and allowed to dry. The Dow compound is a dimethylsilicone polymer that has an infinite molecular weight when cross-linked. This procedure was repeated until the fiber's distal face was coated with a light-pink layer, approximately 10-50 um thick as observed with a microscope. The delicate distal end of the fiber was fitted with a light impermeable, porous, stainless steel sheath to protect the sensing layer.

Figure 5:
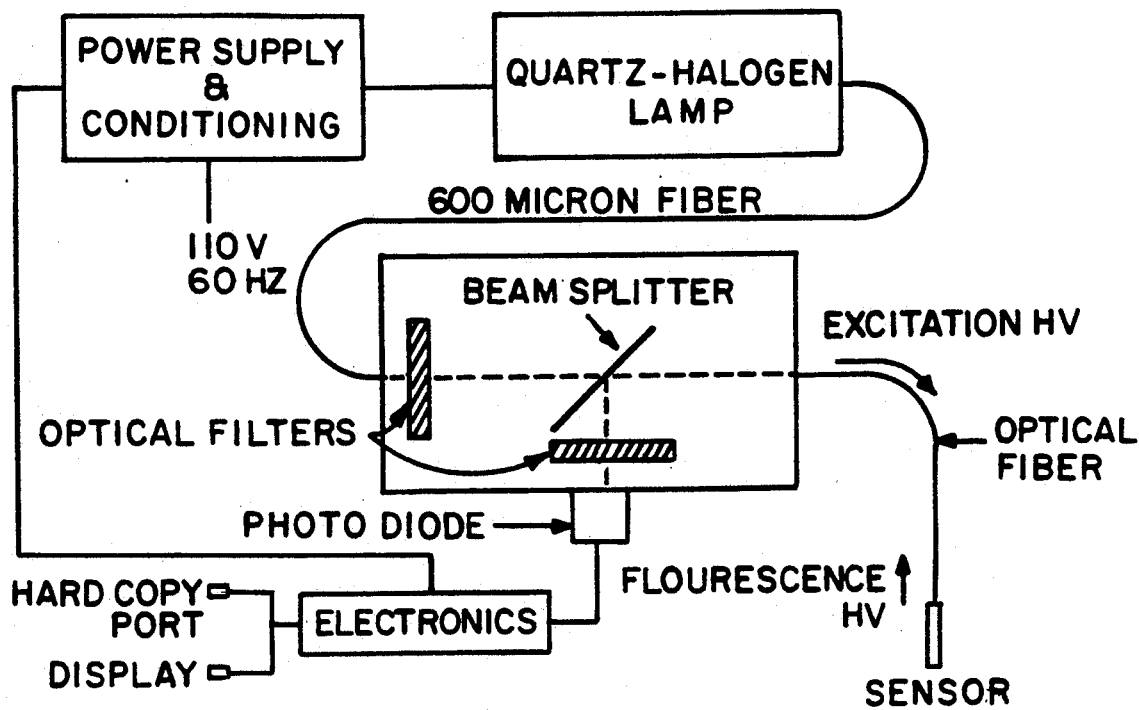
FIG. 5 is a block diagram of a field-portable fluorometer.

Field-Portable Instrumentation: A block diagram of an apparatus constituting the portable hydrocarbon fluorometer is shown in FIG. 5. The illuminating light from a quartz halogen lamp was focused into a 600 um diameter fiber and conducted to an optical coupler, where the appropriate excitation wavelength was selected by a 540 nm bandpass filter. A beam splitter was used to discriminate and direct returning fluorescence light through a 600 nm longpass filter before it impinged on a photodiode. The signal was conditioned electronically and output to a hard-copy port. The instrument was packaged into an aluminum case, having the dimensions 46 cm long × 36 cm wide × 18 cm high, weighing 13 kg, requiring 100 V, 60 Hz power for operation.

Measurements: The laboratory data were collected with both a research grade fiber-optic fluorometer [Luo, S. and D. R. Walt, *Anal. Chem.* 61:174-177 (1989)] and the field-portable fluorometer. All samples were measured, except those in the field, by a static headspace technique [Roe et al., *Anal. Chem.* 61:2584-2585 (1989)]. All measurements are of the headspace above the aqueous phase. Single-component standard solutions were prepared by dissolving the appropriate amount (micrograms) of aromatic hydrocarbon in 1 L of distilled water. A 250 mL volume of standard solution was added to a 400 mL glass jar, leaving a headspace volume of 150 mL. The ratio (0.60) of headspace volume to sample volume was kept constant in all measurements. The jars were fitted with a cover containing an air-tight rubber septum. To measure each sample, the sensor was pushed through the septum, exposing the sensor's tip to the organic vapor partitioned in the headspace volume. The baseline fluorescence was recorded in a sampling vial containing only distilled water. The voltage of the photodiode was recorded over time from a digital display. All laboratory samples were tested at a constant 25° C. by using a thermostated bath to obtain constant vapor pressure. Field data were collected in cooperation with Morlock Environmental (Lebanon, N.H.) at Pease Air Force Base, Dover, N.H.

Selection of Fluorophore-Polymer Combination: The optical properties of Nile Red allow it to be used readily in the detection of organic compounds. It has been used commonly as a lipophilic dye in staining cells and membranes and as a solvent polarity indicator. Although its solvachromic behavior has been described, it has not been investigated extensively. Its fluorescence excitation and emission maxima vary with the hydrophobicity of its microenvironment. For example, the emission maxima of Nile Red in heptane and acetone are 525 and 605 nm, respectively. These optical properties may be exploited by creating a microenvironment that is sensitive and susceptible to changes in hydrophobicity.

Silicone polymers are highly permeable to gases and organic solvents [Kesting, R. E., *Synthetic Polymer Membranes: A Structural Perspective*, Chapter 4, Wiley & Sons, New York, 1985]. Therefore, an organic-vapor sensing layer can be constructed by incorporating Nile Red into a thin siloxane polymer layer on the distal face of an optical fiber. As the polymer layer is exposed to organic vapors, absorption causes the microenvironment of Nile Red to become more nonpolar, resulting in fluorescence enhancement of the fluorophore.

Figure 6:
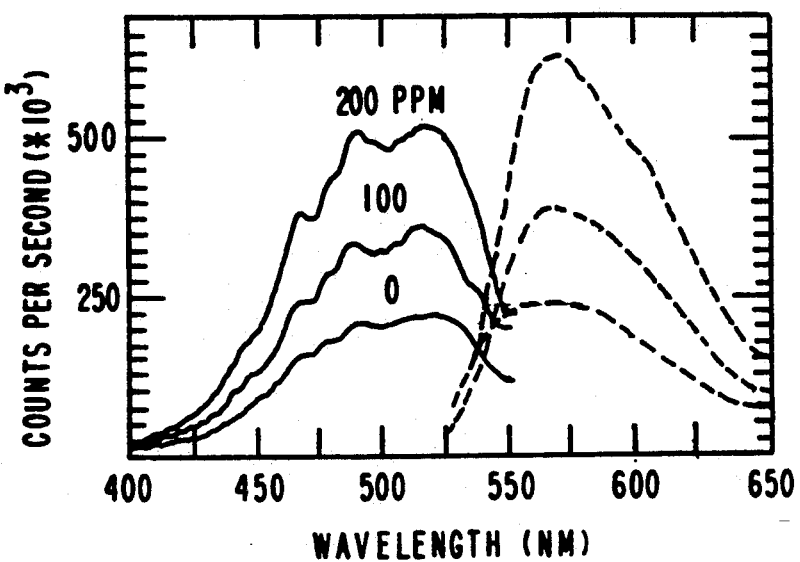
FIG. 6 is a graph illustrating the excitation and emission spectra of a sensor exposed to benzene.

Spectral Characteristics: FIG. 6 displays the increase in intensities of both the excitation and emission spectra of a sensor placed in the headspace above three different concentrations of benzene acquired with the research instrument; and show the excitation and emission spectra of a sensor exposed to 0, 100, and 200 ppm benzene. The excitation spectra were collected by scanning the excitation monochromator from 400 to 550 nm and monitoring the emission at 580 nm. The emission spectra were collected by measuring the emission from 530 to 650 nm, using an excitation wavelength of 500 nm. These spectra were taken by the method of sampling described under Measurements. The emission signal increases from 238,000 cps in 0 ppm benzene to 625,000 cps in 200 ppm benzene. This dramatic increase in intensity is caused by absorption of benzene into the polymer microenvironment of Nile Red, resulting in enhanced fluorescence.

Moreover, the fluorescence emission maximum shifts from approximately 560 to 570 nm, corresponding to the solvachromic sensitivity of Nile Red. This shift could be attributed to the benzene-absorbed polymer microenvironment stabilizing the excited state of the fluorophore, shifting the wavelength maximum to lower energy and, therefore, longer wavelengths. This effect is consistent with stabilization of the excited state in $n-\pi^*$ or $\pi-\pi^*$ electronic transitions.

Figure 7:
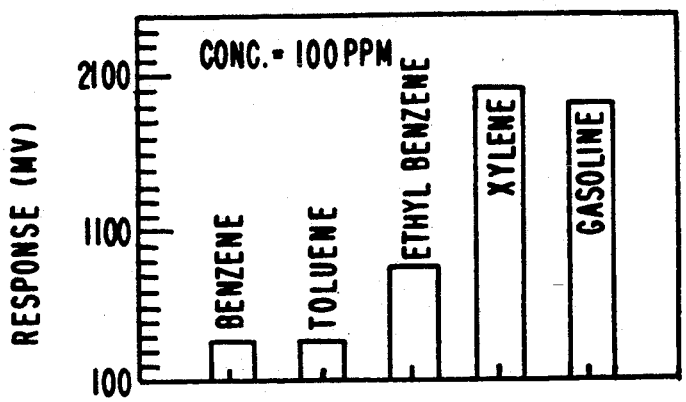
FIG. 7 is a graph illustrating the sensor responses to a BTEX series and gasoline.

General Response Characteristics: FIG. 7 shows the responses of a sensor to the individual components of the conventional BTEX series (benzene, toluene, ethylbenzene, xylene) and unleaded gasoline at 100 ppm with the field portable instrument. The concentration of gasoline, being a multicomponent species, is defined as the number of microliters of gasoline per liter of water. No attempt was made to calculate the vapor-phase concentration. Although the sensor is most sensitive to xylene in the BTEX series, it responds equally well to gasoline, indicating that the sensor responds generally to a wide variety of volatile organic vapors. These unequal responses to the BTEX series cannot be explained by the differences in vapor pressure of the BTEX series components, but are most likely due to differences of the individual compounds in their permeability coefficients and solubilities in the polymer.

Figure 8:
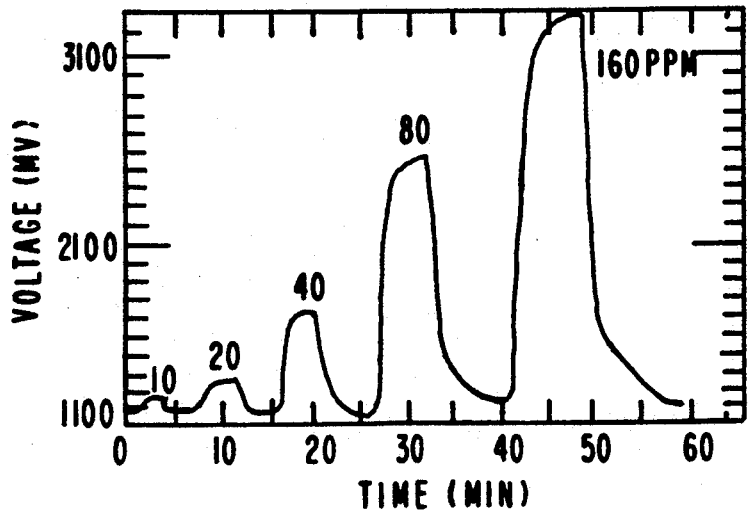
FIG. 8 is a graph illustrating the sensor's response to xylene over time.

A typical sensor response to increasing concentrations of p-xylene as a function of time can be seen in FIG. 8. The baseline response was measured in the headspace of a flask containing only distilled water. When the sensor is placed in a flask containing p-xylene, a sharp rise in voltage occurs, followed by a slower leveling off as equilibrium is established between the headspace and sensing-layer vapor concentrations. FIG. 8 indicates that the sensor response time is established in less than 2.5 minutes as defined by the signal reaching 90% of its final value. The recovery times, defined by the signal decreasing to within 10% of the starting baseline values, are longer; for example, for 10 and 160 ppm the recovery times are 2.5 and 10 minutes, respectively. The desorption process is retarded probably by nonspecific hydrophobic interactions between the absorbed organic vapor and the hydrophobic polymer/dye layer. The rate-determining process is the diffusion of the vapor into and out of the polymer layer, restricting the sensor's response and dictating the frequency of sampling.

Figure 9:
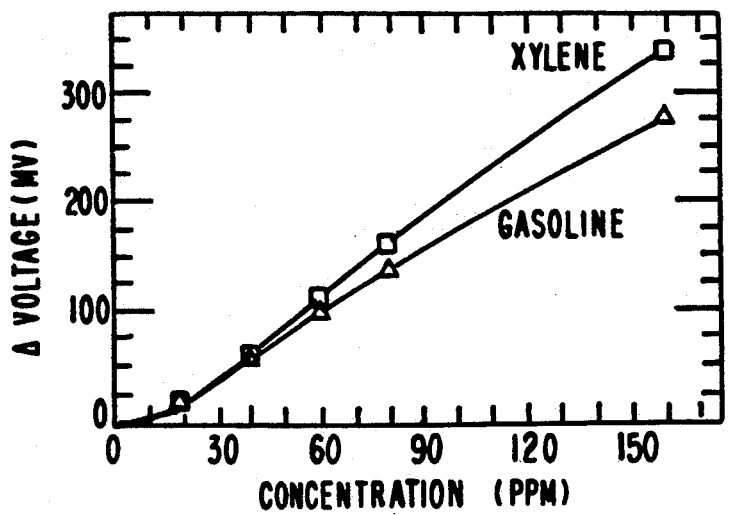
FIG. 9 is a graph showing the sensor's calibration curves of xylene and gasoline at varying concentration.

FIG. 9 shows calibration curves for xylene and gasoline, indicating very good linearity in the concentration range of 10–160 ppm. The variation in slopes is due to sensitivity differences of the sensor to xylene and gasoline. Below 10 ppm, vapor detection is possible, but nonlinear behavior is observed. The sensor can detect 1 ppm gasoline but cannot be used to make quantitative measurements due to the nonlinearity of the calibration curve in this region. However, it is still very useful in situations that require information as to the presence or absence of a contaminant, such as in leak detection from underground storage tanks.

Temperature Dependence: The sensor response is related directly to the vapor pressure of the organic component. During data collection on the samples investigated above, a constant temperature was maintained throughout the measurement process.

Figure 10:
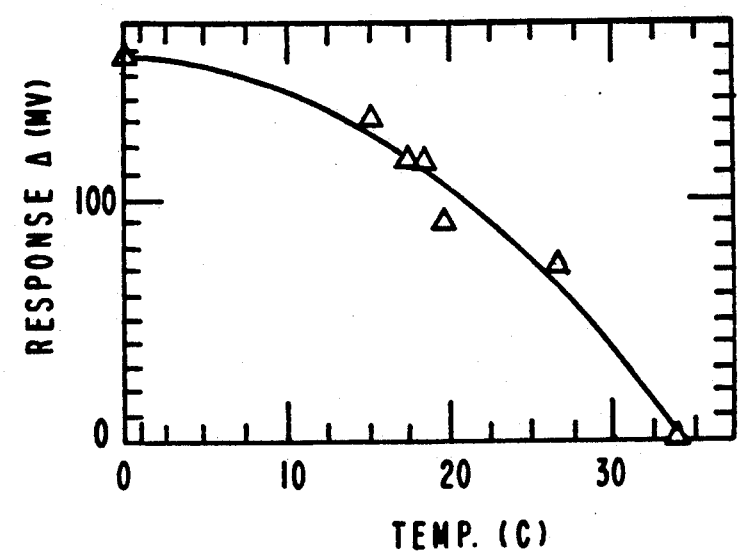
FIG. 10 is a graph illustrating the sensor's temperature dependence of baseline signal.
Figure 11:
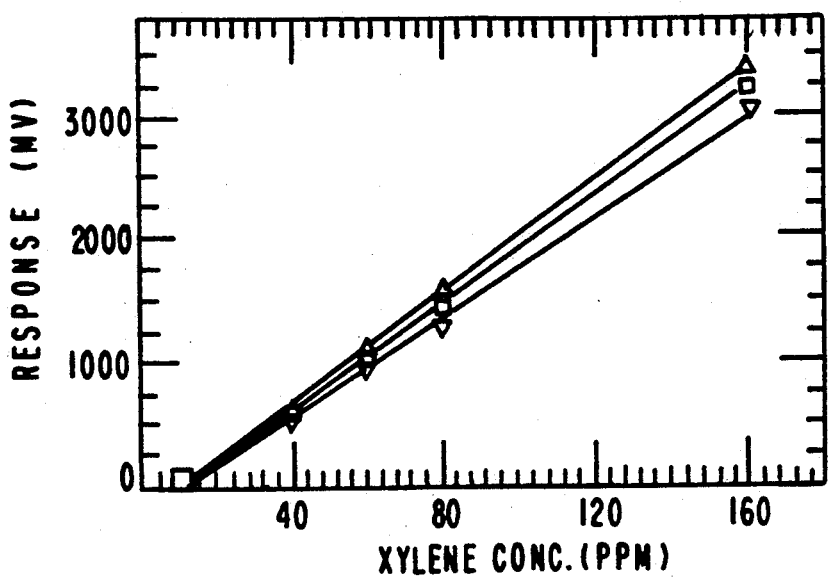
FIG. 11 is a graph illustrating the sensor's temperature dependence of xylene calibration at 25° C., 30° C., and 35° C.

To investigate the effect of temperature on the baseline signal, a sensor was placed in a sampling vial containing only distilled water and was submerged into a temperature-controlled water bath. As expected, the fluorescence signal decreased due to acceleration of the thermal relaxation processes as the temperature was raised from 4° to 30° C. as shown in FIG. 10. In contrast, in the presence of xylene vapor, the sensor shows an increase in response as temperature increases. This is illustrated by FIG. 11. This result can be explained by four effects influencing sensor response simultaneously. First, the vapor pressure of the organic component increases with temperature, providing a greater headspace concentration. Second, the polymer layer structure may become more amorphous, causing a decrease in porosity and a greater exclusion of water vapor. Water vapor could act as an interference by increasing the polarity of the membrane. Third, in most cases, higher operating temperatures increase the permeability coefficient and decrease the activation energy of the diffusion process. Fourth, is the temperature dependence of the fluorophore.

Figure 12:
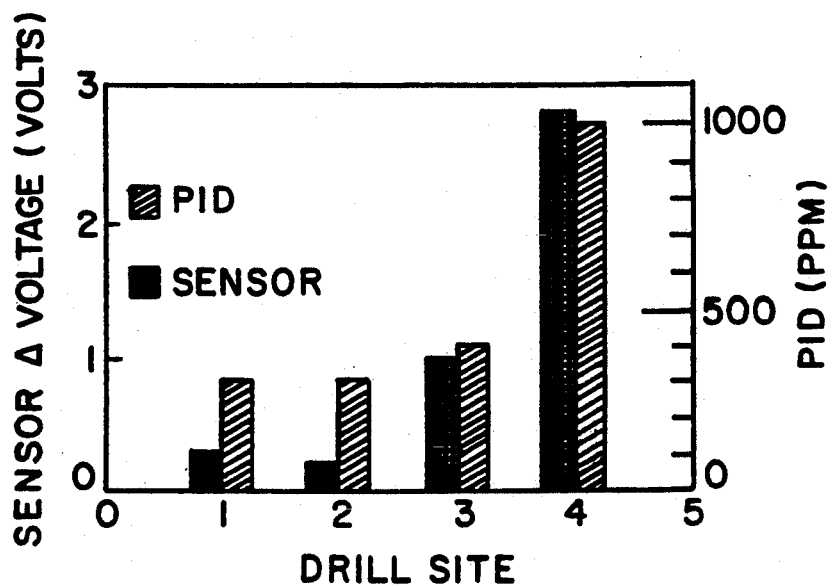
FIG. 12 is a graph illustrating field data analyses at four different wells contaminated with jet fuel.

Initial Field Data: The purpose of the initial field work was to show that the sensor responds qualitatively to in-situ field concentrations and that the system was field-hardened. No attempt was made to critically evaluate the sensor's performance with that of established field methods (i.e., gas chromatography or photoionization probe (PID)). The field studies were performed in cooperation with Morlock Environmental and were conducted at Pease Air Force Base, NH, at a site contaminated with JP4 jet fuel. Four individual wells were measured in-situ with the fiber-optic sensor and its supporting instrumentation and these measurements were compared to simultaneous readings from a portable Photovac TIP PID, with a 10.2-eV lamp. The PID measurements were used as a relative indicator of contamination between sites, allowing us to test the response of the sensor to in-situ samples of different concentrations. The sensor was calibrated with benzene by the method described under Measurements and the PID was spanned between air and 100 ppm (aqueous solution) benzene standard. Thus, the reported values in FIG. 12 for the PID are "benzene equivalents," which should approximate the extent of contamination in each well. FIG. 12 shows the response of a sensor in each well at a depth of 3.5 m below ground level, compared to concentrations measured concurrently with the PID. The PID measurements indicate that the four drill sites have varying degrees of contamination. The fiber-optic sensor responded comparably to in-situ concentrations of JP4 in each monitoring well. Moreover, the sensor responded semiquantitatively to the different degrees of contamination as defined by the PID.

Attempts to compare critically the measurements between the two instruments must be preceded by a thorough investigation taking into account the various problems of calibration and sampling. For example, PIDs are compound-dependent, being more sensitive to aromatics than aliphatics. On the other hand, the sensor is less compound dependent because it is based on analyte polarity. Therefore, any comparison must account for this calibration disparity. The calibration issue is especially important in monitoring multicomponent contamination sites. Since JP4 is composed of alkanes, alkenes, and aromatics, the response would depend on the sensitivity of the sensor both to the individual components and to the components collectively.

The approach of using a microenvironmentally sensitive fluorophore and organic vapor permeable polymer as a sensing mechanism has proven successful in the laboratory and from initial field studies. The sensor responds to environmentally significant levels of light mononuclear aromatics (BTEX series) and gasoline in the laboratory and responds to in-situ samples of VOCs. From the wide range of compounds studied, the sensor should generally respond to virtually any organic volatile compound. The approach described has several advantages: the sensors are inexpensive to construct and provide true real-time, in-situ measurements; sensors respond almost instantaneously to the presence of VOCs, enabling a large number of samples to be measured; their small size allows smaller diameter sampling wells to be drilled; and sensors can be used in situations where electrical devices pose risks.

V. Alternative Embodiments of the Fiber Optic Sensor

The various polarity-sensitive dye/polymeric material combinations that were used are listed in Table 6. Each successive dye/polymer pair reflects and demonstrates the basic result.

TABLE 6

| Pair | Polarity-Sensitive Dye | Polymeric Material |
|------|------------------------|--------------------|
| 1 | Fluorescein | dissolved parafilm |
| 2 | Acrylodan | dissolved parafilm |
| 3 | Dansyl lysine | dissolved parafilm |
| 4 | Anthracene-9-carboxaldehyde carbohydrazone | dimethyl methylvinyl siloxane |
| 5 | Octadecyl rhodamine | dimethyl methylvinyl silicone |
| 6 | Nile Red | dimethyl |

TABLE 6-continued

| Pair | Polarity-Sensitive Dye | Polymeric Material |
|------|------------------------|--------------------|
| | | silicone |

A. The Acrylodan-Parafilm Combination

Figure 13:
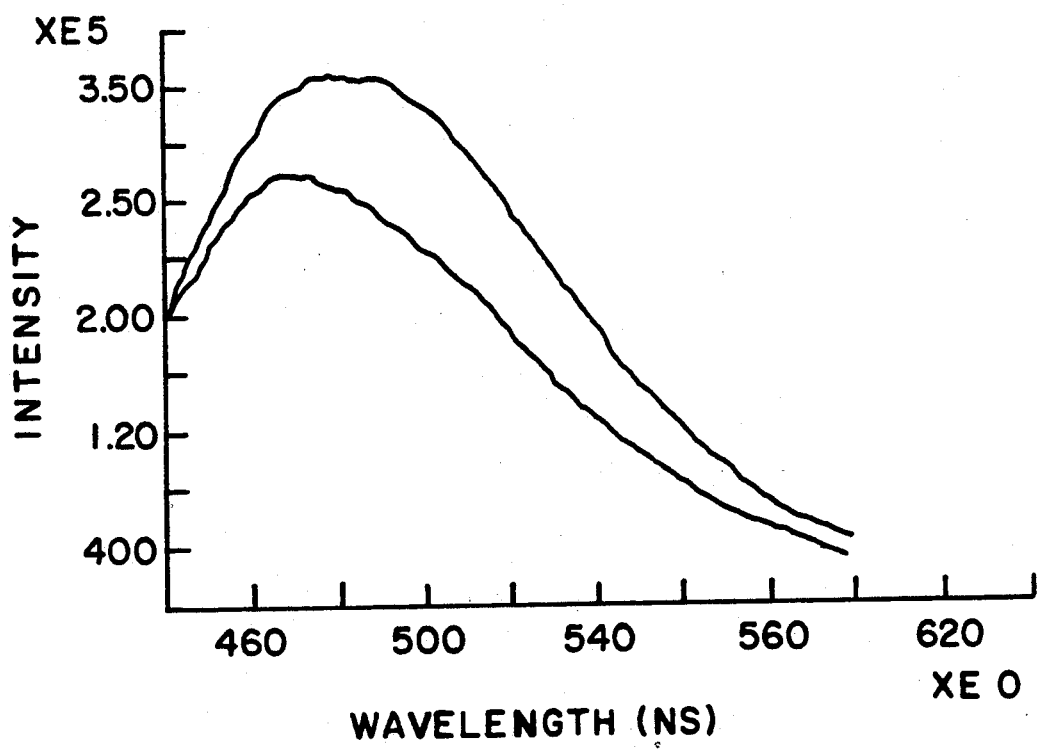
FIG. 13 is a graph illustrating the emission spectrum of an acrylodan/parafilm sensor exposed to toluene vapors.

Using a viscous solution of polymer and dye, a bare optical fiber was dip-coated to produce a thin layer of acrylodan/parafilm. Acrylodan was selected because it is environmentally sensitive and has been used to test ligand binding. Parafilm was used because it is a wax-like substance and allows the absorption of hydrocarbons. Furthermore, it was readily available. FIG. 13 shows the response of the fully constructed acrylodan/parafilm sensor to gasoline exposure. The emission spectrum decreases in intensity on exposure to toluene. This sensor was tested on a xenon arc lamp research grade fiber optic fluorometer. The values given by Table 7 show about a 16% decrease in intensity on exposure to 200 μl of toluene in a 1.0 liter flask of air.

| VALUES OF THE ACRYLODAN/PARAFILM SENSORS EXPOSED TO TOLUENE | | |
|---|---|---|
| Concentration | Time | Kcps |
| 0 | 1 | 208 |
| | 2 | 204 |
| | 3 | 207 |
| | 4 | 204 |
| 200 | 5 | 167 |
| | 6 | 173 |
| | 7 | 170 |
| | 8 | 169 |
| 0 | 9 | 182 |
| | 10 | 197 |
| | 11 | 195 |
| | 12 | 195 |
| 200 | 13 | 168 |
| | 14 | 189 |
| | 16 | 180 |
| | 15 | 186 |
| 0 | 17 | 228 |
| | 18 | 229 |
| | 19 | 232 |
| | 20 | 238 |
| 200 | 21 | 215 |
| | 22 | 215 |
| | 23 | 216 |
| | 24 | 216 |

B. The Dansyl Lysine-Parafilm Combination

Figure 14:
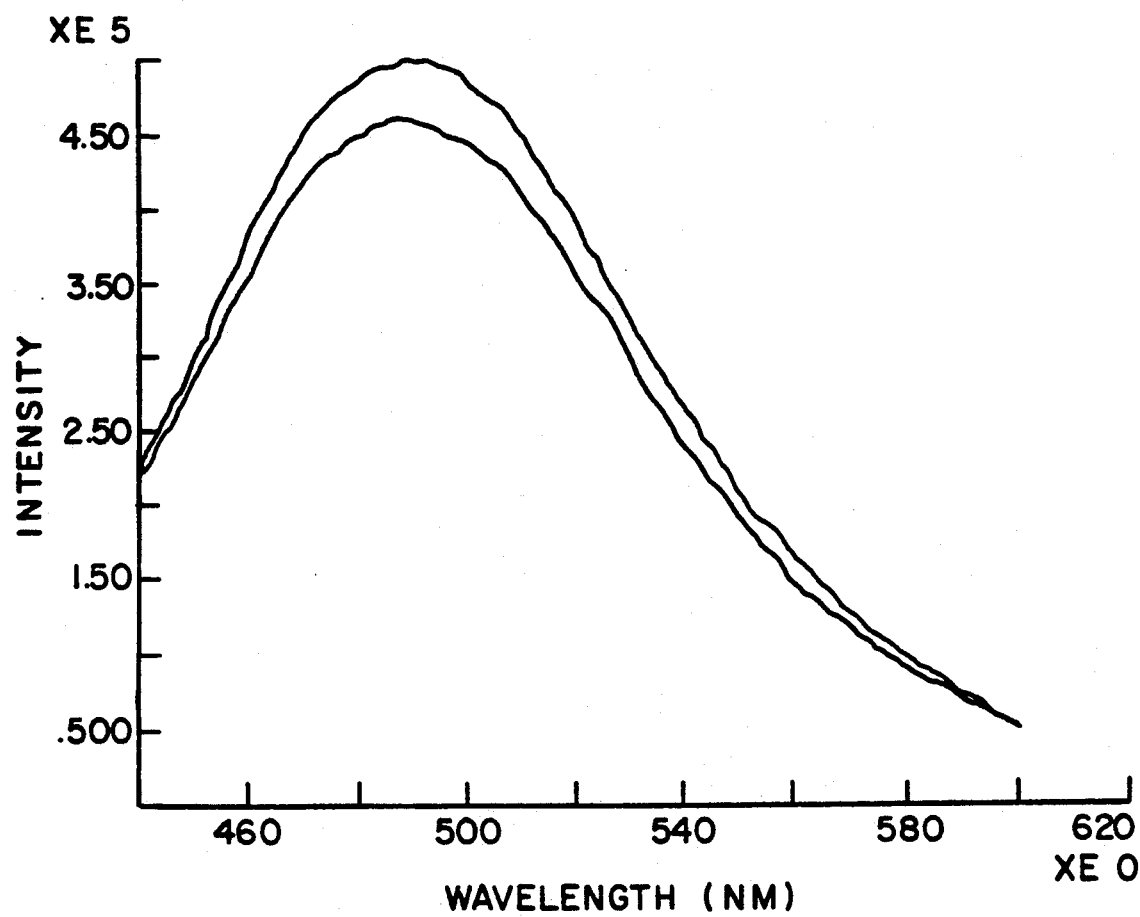
FIG. 14 is a graph illustrating the emission spectrum of a donsyl/parafilm sensor exposed to toluene.

FIG. 14 empirically shows that the fluorescence of the solvachromic dye decreases on exposure to pure toluene. This combination suffered from the same troubles as the previous acrylodan/parafilm signal sensor—such as poor solubility in the polymer; weak fluorescence; and a decreased signal on exposure to organic vapor. The data of FIG. 14 shows the emission spectrum of a dansyl lysine/parafilm sensor exposed to toluene.

Figure 15:
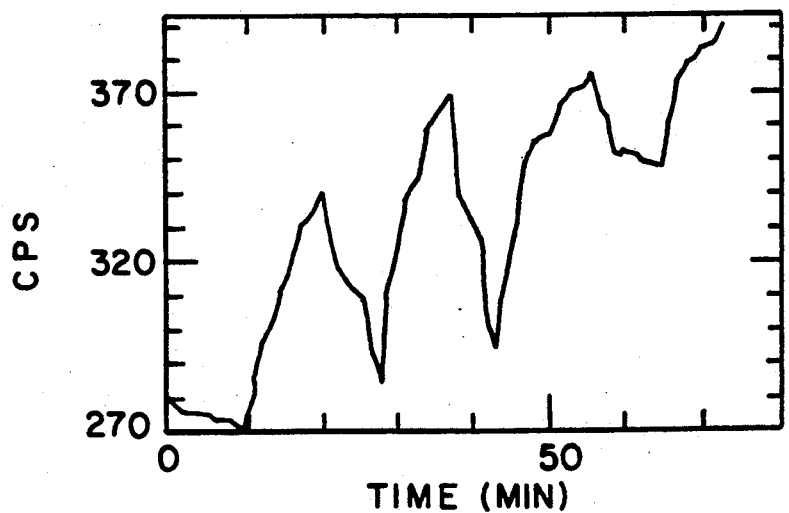
FIG. 15 is a graph illustrating the response of an anthracene-9-carboxyaldehyde carbohydrazone/-dimethyl and methyl vinyl siloxane sensor to toluene.

C. The Anthracene-9-Carboxyaldehyde Carbohydrazone/Dimethyl and Methylvinyl Silicore Combination A third solvachromic fluorophore, anthracene-9-carboxaldehyde carbohydrazone or "ACC" was used first with parafilm and then with a gas chromatography copolymer, dimethylsiloxane and methylvinylsiloxane. The empirical results shown by FIG. 15 shows the response of a sensor made out of the copolymer when exposed to 333 μl of toluene in 1.0 liter of air. It was evident that the large increase in signal, averaging 14%, was a vast improvement that could be attributed to the change in polymer.

D. The Octadecyl Rhodamine/Dimethyl and Methylvinyl Silicone Combination

It was deemed that a lipophilic dye would be a better choice of solvachromic fluorophore due to its improved solubility in organic solvents and desirable solvachromic behavior. The first lipophilic dye evaluated was octadecyl rhodamine B chloride salt or "ODR". This lipophilic dye has several advantages over dyes tested previously: it has a greater solubility in organic solvents; it does not partition out of the polymer due to its long octadecyl tail; it has excitation and emission peaks at longer wavelengths (ex 540, em 580); and it has good photostability.

Figure 16:
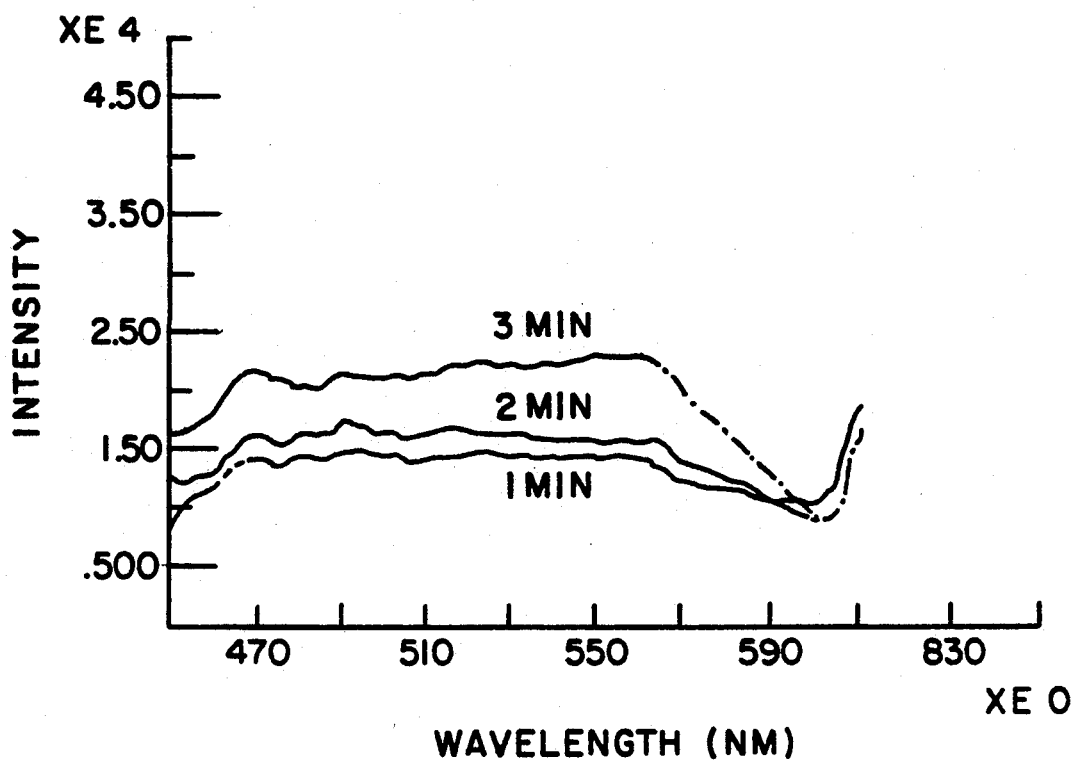
FIG. 16 is a graph illustrating the excitation spectrum of octadecylrhodamine in the copolymer dimethyl and methyl vinyl siloxane for the sensor on exposure to gasoline at different time intervals.
Figure 17:
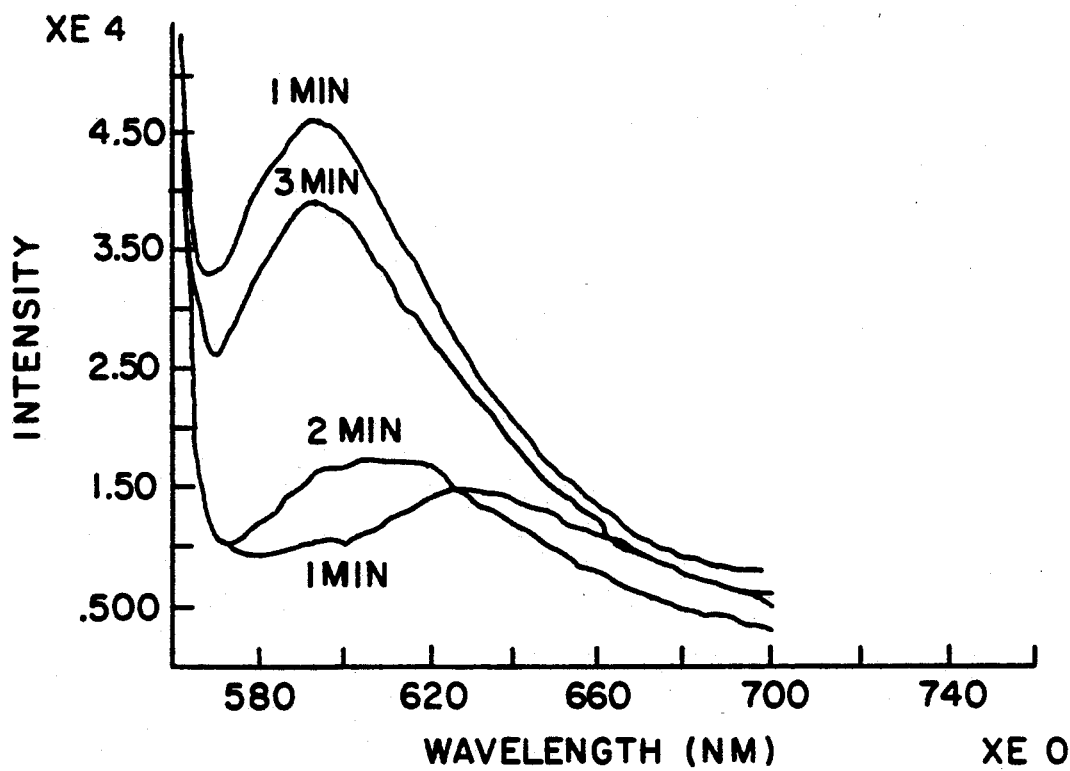
FIG. 17 is a graph illustrating the emission spectrum of octadecyl rhodamine (ODR) in the copolymer dimethyl and methyl vinyl siloxane (DMMV) for the sensor on exposure to gasoline at different time intervals.

Spectral Characteristics: The excitation and emission spectra of ODR in the polymer are shown in FIGS. 16 and 17. FIG. 16 shows the excitation spectrum of octadecylrhodamine in the copolymer dimethyl and methyl vinyl siloxane on exposure to gasoline (100 ul of gasoline in 1 liter of air) taken at different time intervals: (1) after 1 minute; (2) after 2 minutes; and (3) after 3 minutes. In comparison, FIG. 17 shows the emission spectrum of octadecylrhodamine in the copolymer dimethyl and methylvinyl siloxane on exposure to gasoline taken at different time intervals (100 ul of gasoline in 1 liter of air): (1) after 1 minute; (2) after 2 minutes; (3) after 5 minutes; and (4) after 7 minutes.

On exposure to gasoline, the excitation and emission spectra both increase in intensity. After seven minutes the photon intensity increased from 15,000 to 45,000 counts per second. This increase is believed attributable to the increased sensitivity of ODR to changes in its microenvironment. The maximum emission wavelength was shifted from 630 nm to 590 nm, indicating that ODR's solvachromic behavior is preserved in the polymer.

Figure 18:
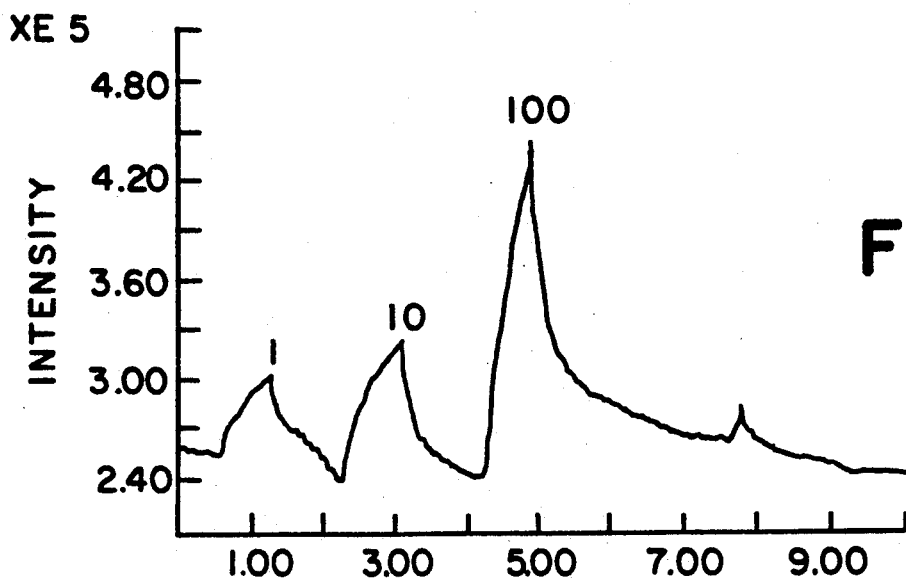
FIG. 18 is a graph illustrating the response profile of ODR/DM MV siloxane in a sensor exposed to toluene.

Response Characteristics:

The response profile of an ODR/DM MV siloxane sensor to three concentrations of toluene is shown in FIG. 18. An immediate increase in intensity occurred on exposure to vapor; and after one minute the sensor was withdrawn from the sample and the intensity returned to initial baseline values. This proves that the polymer absorption process essentially is reversible.

Figure 19A:
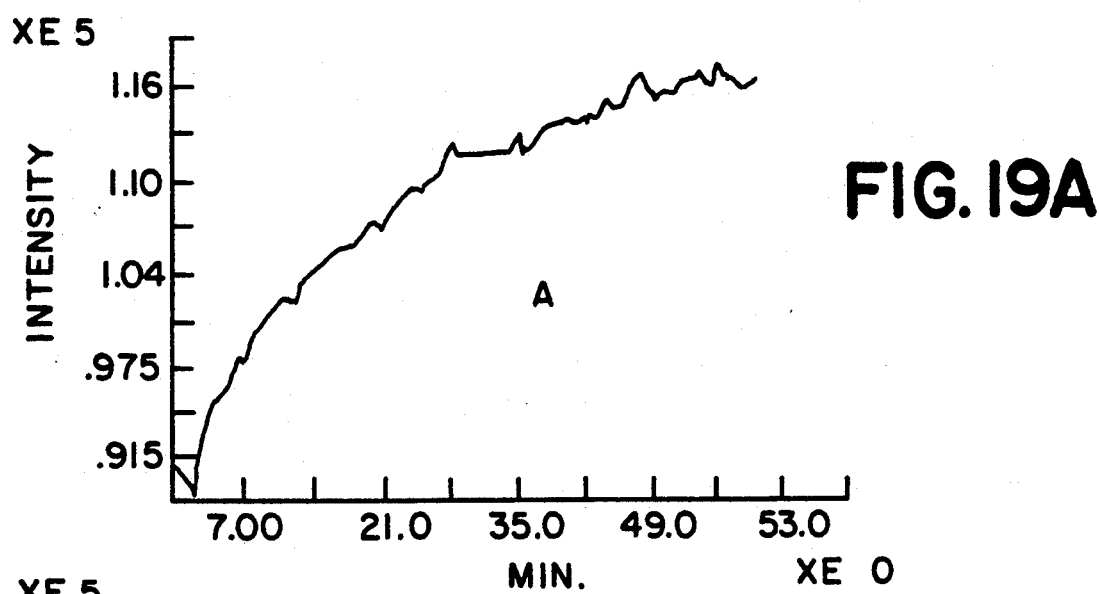
FIGS. 19A–19C are graphs showing the response values of ODR/DM MV siloxane in a sensor exposed to varying volumes of gasoline in air.
Figure 19B:
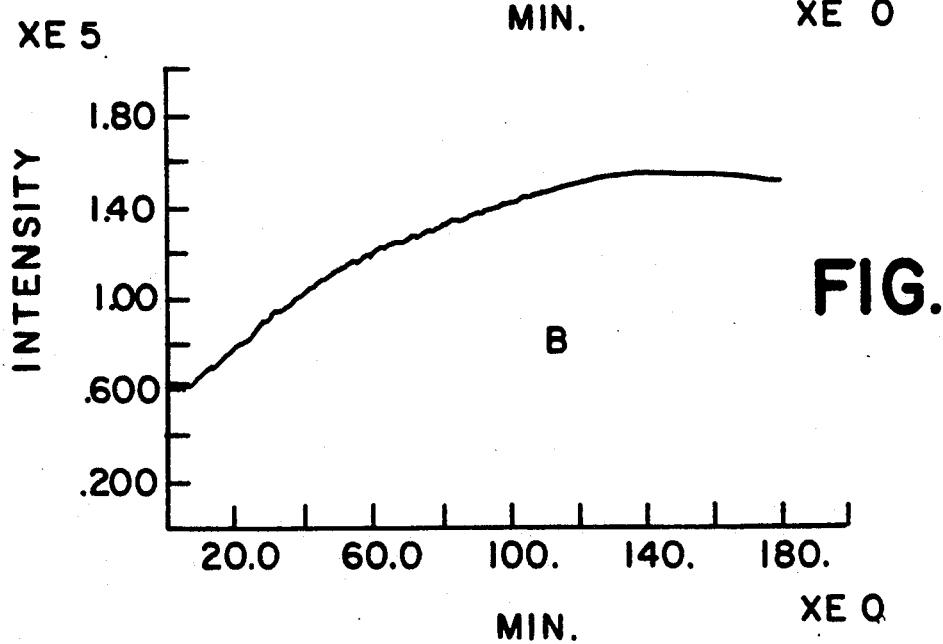
Figure 19C:
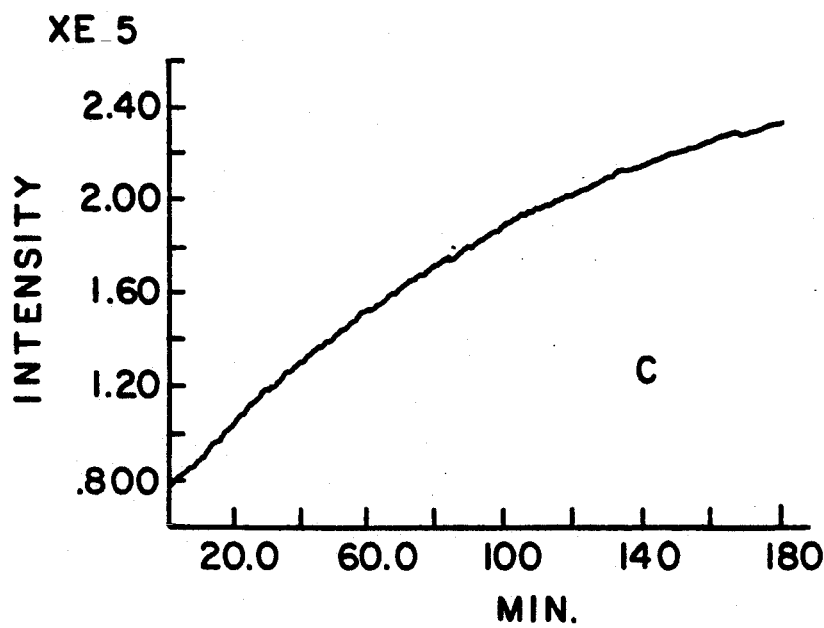
Figure 20:
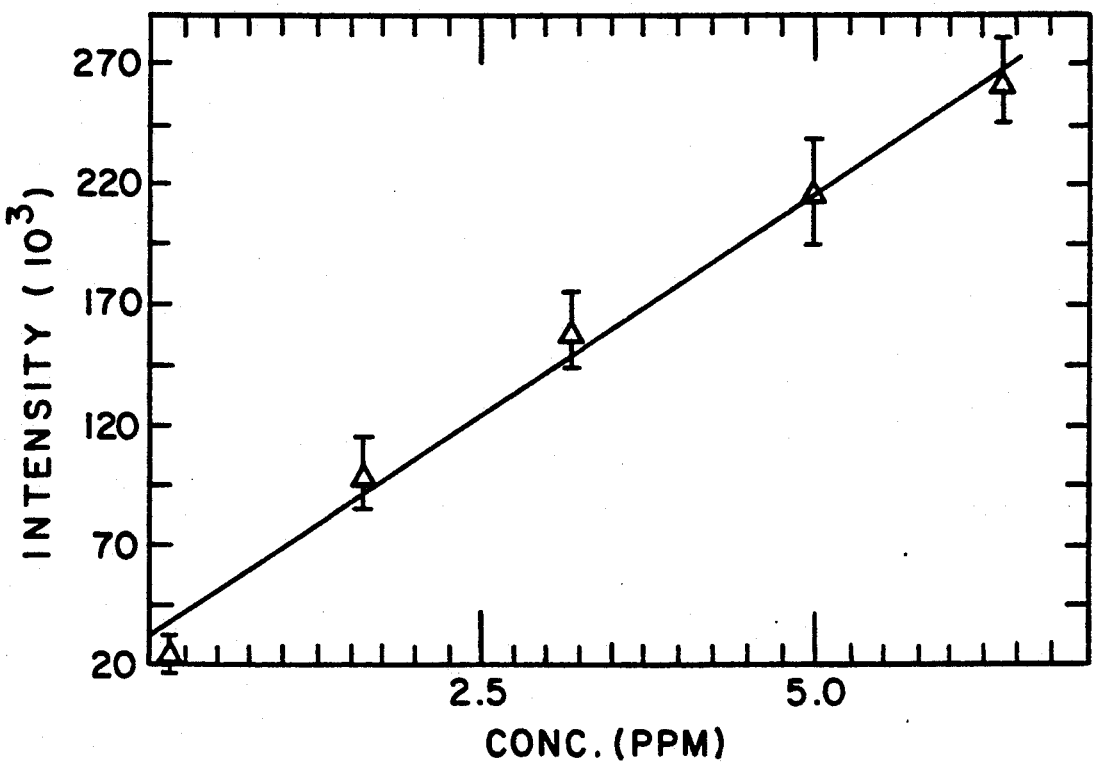
FIG. 20 is a graph illustrating the calibration curve of an ODR/DM MV siloxane sensor.

FIGS. 19A-19C show the response of this sensor to three different concentrations of gasoline. FIG. 19A shows exposure to 1 ul gasoline in 6 liters of air; FIG. 19B shows exposure to 10 ul gasoline in 6 liters of air; and FIG. 19C shows exposure to 20 ul gasoline in 6 liters of air. As the sensor is exposed to organic vapor, the intensity rises, reaching a plateau at 49 minutes for 0.16 ppm, 110 minutes for 1.6 ppm, and over 180 minutes for 3.2 ppm, indicating equilibrium conditions have been achieved across the membrane. The equilibrium intensity values can be used to generate a calibration plot as shown by FIG. 20. The data are the mean standard deviation of three measurements.

The curve was fitted to the equation: $Y = 3.06 \times 10^4 + X\, 3.75 \times 10^4$. Because the time to reach equilibrium is relatively long, a kinetic calibration plot can quantitate concentration.

Figure 21:
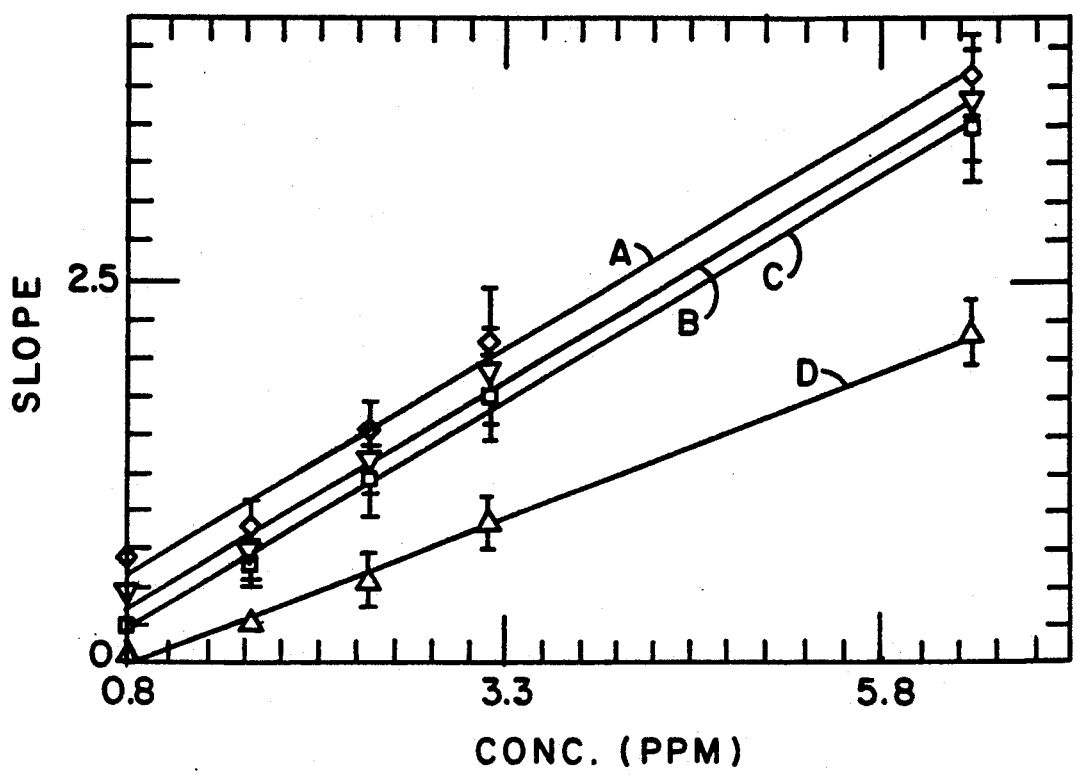
FIG. 21 is a graph illustrating slope calibration measured after 90 minutes of four different ORD/DM MV siloxane sensors.

In comparison, FIG. 21 illustrates slope calibration measured after 90 minutes of four different ODR/DM MV siloxane sensors. The data are the mean standard deviation of three measurements. The data were fitted to the equations-Curve A: $Y = -1.78 \times 10^{-1} + X\, 5.77 \times 10^{-1}$; curve B: $Y = -1.78 \times 10^{-1} + X\, 5.80 \times 10^{-1}$; curve C: $Y = -5.83 \times 10^{-2} + X\, 5.85 \times 10^{-1}$; curve D: $Y = -2.98 \times 10^{-1} + X\, 3.78 \times 10^{-1}$. Note that FIG. 21 shows the changes in slope that occur over the first 60 minutes of exposure are responsive to the different concentration of gasoline used.

Figure 22:
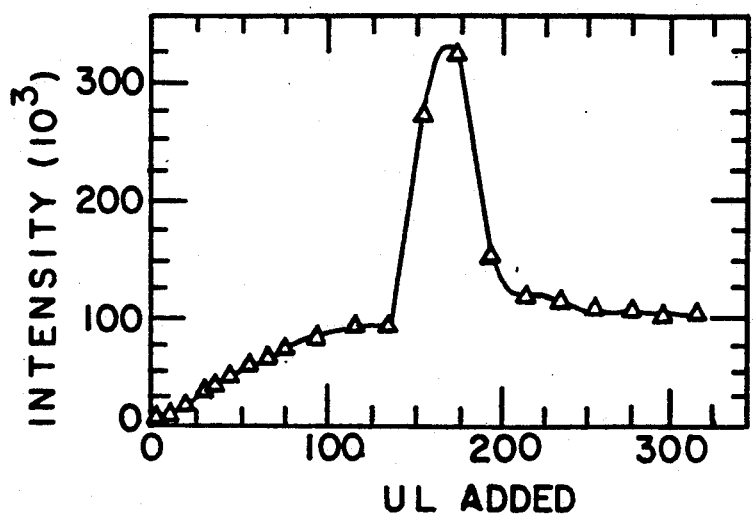
FIG. 22 is a graph illustrating the optimal dye concentration for maximum fluorescence in an ORD/DM MV siloxane sensor.

It was deemed important to work with dye concentrations that produced strong fluorescence signals; and to identify those which were most sensitive to small changes in the concentration of absorbed vapor. To test for maximum response, a highly concentrated solution of solvachromic dye was serially diluted by adding aliquots of gasoline. FIG. 22 shows dye concentration as a function of fluorescence signal and demonstrates a maximum intensity at a dilution corresponding to $1.15 \times 10^{-3}$ M/L. The dye concentration that produces the largest signal change with the smallest change in exposure corresponds to the concentration in FIG. 22 at the left edge of the peak: $1.7 \times 10^{-3}$ M/L. Table 8 shows the average ratio change on exposure to acetone of five different groups of sensors made with an increasing concentration of dye. The increase in ratio indicate the dye concentration of dye. The increase in ratio indicate the dye concentration in the polymer is important and should be optimized. The data acquired on ODR-DM MV siloxane combination demonstrated conclusively that the sensor was both operational and capable of continuous monitoring.

TABLE 8

SENSOR RATIO DATA OF OPTIMUM DYE CONCENTRATION

| Group | Dye Concentration Molar ($10^{-3}$) | Average Ratio $I_x/I_o$ |
|---|---|---|
| A | 0.5 | 1.26 |
| B | 1.0 | 1.17 |
| C | 1.7 | 1.34 |
| D | 2.5 | 1.2 |
| E | 4.0 | 1.1 |

Sensors were exposed to pure acetone. The ratio is $I_x/I_o$ ($I_x$ is the intensity on exposure to acetone and $I_o$ is the intensity before exposure.

The present invention is not to be restricted in form nor limited in scope except by the claims appended hereto.

What is claimed is:

1. A fiber optic sensor for detecting an organic analyte of discernible polarity in a fluid sample, said fiber optic sensor comprising:

an optical fiber strand able to convey light energy of a predetermined wavelength, said optical fiber strand having a proximal end, a distal end, and a strand length;

at least one polarity-sensitive dye immobilized at the distal end of said optical fiber strand, said at least one polarity-sensitive dye being able to absorb light energy of a predetermined wavelength and change its spectral properties upon exposure to an entity of discernible polarity; and at least one polymeric material immobilized at the distal end of said optical fiber strand in a manner such that said at least one immobilized polarity-sensitive dye is contained within and is surrounded by said at least one polymeric material and the spectral properties of said at least one contained polarity-sensitive dye are mediated by said surrounding at least one immobilized polymeric material, through which at least a portion of such organic analyte of discernible polarity as is presented by a fluid sample becomes absorbed and at least partially partitioned by said at least one immobilized polymeric material concomitant with making reactive contact with said at least one contained polarity-sensitive dye and a detectable change in the spectral properties of said at least one contained polarity-sensitive dye is produced as a consequence of such reactive contact.

2. A fiber optic sensor for detecting an organic analyte of discernible polarity in a fluid sample, said fiber optic sensor comprising:

an optical fiber strand able to convey light energy of a predetermined wavelength, said optical fiber strand having a proximal end, a distal end, and a strand length;

at least one polarity-sensitive dye immobilized at the distal end of said optical fiber strand, said at least one polarity-sensitive dye being able to absorb light energy of a predetermined wavelength and change its spectral properties upon exposure to an entity of discernible polarity;

at least one polymeric material immobilized at the distal end of said optical fiber strand in a manner such that said at least one immobilized polarity-sensitive dye is contained within and is surrounded by said at least one polymeric material and the spectral properties of said at least one contained polarity-sensitive dye are mediated by said surrounding at least one immobilized polymeric material, through which at least a portion of such organic analyte of discernible polarity as is presented by a fluid sample becomes absorbed and at least partially partitioned by said at least immobilized polymeric material concomitant with making reactive contact with said at least one contained polarity-sensitive dye and a detectable change in the spectral properties of said at least one contained polarity-sensitive dye is produced as a consequence of such reactive contact;

means for introducing light energy of a predetermined wavelength to the proximal end of said optical fiber strand; and means for detecting light energy conveyed from said at least one contained polarity-sensitive dye.

3. The fiber optic sensor as recited in claim 1 or 2 wherein said optical fiber strand conveys exciting light energy of a first wavelength and emitted light energy of a second wavelength.

4. The fiber optic sensor as recited in claim 1 or 2 wherein said at least one polarity-sensitive dye is a chromophore.

5. The fiber optic sensor as recited in claim 1 or 2 wherein said at least one polarity-sensitive dye is a fluorophore.

6. The fiber optic sensor as recited in claim 1 or 2 wherein said at least one polymeric material is a silicone based polymer.

7. The fiber optic sensor as recited in claim 6 wherein said contained at least polarity-sensitive dye is Nile Red.

8. The fiber optic sensor as recited in claim 1 or 2 wherein said at least one polymeric material is selected from the group consisting of polyethylene, polypropylene, polymethylmethacrylate, polystyrene, polyhydroxyethylmethacrylate, polyurethanes, polyvinyl chlorides, polyvinylidene chloride, fluorinated polyolefins, parafilm, and chlorofluoro polyolefins.

9. The fiber optic sensor as recited in claim 2 wherein said means for detecting light energy allows for detection of emitted light energy of another wavelength.

10. A method for detecting an organic analyte of discernible polarity in a fluid sample, said method comprising the steps of:

admixing a fluid sample comprising an organic analyte of discernible polarity with a fiber optic sensor comprised of:

(a) an optical fiber strand able to convey light energy of a predetermined wavelength, said optical fiber strand having a proximal end, a distal end, and a strand length;

(b) at least one polarity-sensitive dye immobilized at the distal end of said fiber optic strand, said at least one polarity-sensitive dye being able to absorb light energy of a predetermined wavelength and change its spectral properties upon exposure to an entity of discernible polarity, and (c) at least one polymeric material immobilized at the distal end of said optical fiber strand in a manner such that said at least one immobilized polarity-sensitive dye is contained within and is surrounded by said at least one polymeric material and the spectral properties of said at least one contained polarity-sensitive dye are mediated by said surrounding at least one immobilized polymeric material, through which at least a portion of such organic analyte of discernible polarity as is presented by the fluid sample becomes absorbed and at least partially partitioned by said at least one immobilized polymeric material concomitant with making reactive contact with said at least one contained polarity-sensitive dye and a detectable change in the spectral properties of said at least one contained polarity-sensitive dye is produced as a consequence of such reactive contact;

introducing light energy of a predetermined wavelength to the proximal end of said fiber optic sensor whereby said light energy is conveyed to said distal end of said optical fiber strand and said at least one contained polarity-sensitvie dye absorbs at lest a portion of said introduced light energy; and detecting light energy conveyed from said at least one contained polarity-sensitive dye of said fiber optic sensor after reactive contact with the fluid sample, said detected light energy being a measure of the organic analyte of discernible polarity in the fluid sample.

11. A method for making a fiber optic sensor able to detect an organic analyte of discernible polarity in a fluid sample, said method comprising the steps of:

obtaining an optical fiber strand able to convey light energy of a predetermined wavelength, said optical fiber strand having a proximal end, a distal end, and a strand length;

admixing at least one polarity-sensitive dye to absorb light energy of a predetermined wavelength and change its spectral properties upon exposure to an entity of discernible polarity with at least one polymerizable material to form a reaction mixture; and polymerizing said reaction mixture at the distal end of said optical fiber strand in a manner such that said at least one polarity-sensitive dye is contained within and is surrounded by an immobilized polymeric material and the spectral properties of said at least one contained polarity-sensitive dye are mediated by said surrounding immobilized polymeric material, through which at least a portion of such organic analyte of discernible polarity as is presented by a fluid sample becomes absorbed and at least partially partitioned by said immobilized polymeric material concomitant with making reactive contact with said at least one contained polarity-sensitive dye and a detectable change in the spectral properties of said at least one contained polarity-sensitive dye is produced as a consequence of such reactive contact.

* * * * *

UNITED STATES PATENT AND TRADEMARK OFFICE
CERTIFICATE OF CORRECTION

PATENT NO. : 5,244,813
DATED : September 14, 1993
INVENTOR(S) : David R. Walt and Steven M. Bernard It is certified that error appears in the above-identified patent and that said Letters Patent is hereby corrected as shown below:

Column 1,
Line 5, after title "FIBER OPTIC SENSOR, APPARATUS, AND METHODS FOR DETECTING AN ORGANIC ANALYTE IN A FLUID OR VAPOR SAMPLE, insert the following paragraph:

-- This invention was made with government support under N00014-94-1-0312 awarded by the Department of the Navy, Office of Naval Reserch. The government has certain rights in the invention. --

Signed and Sealed this

Fourth Day of June, 2002

*Attest:*

JAMES E. ROGAN
*Attesting Officer*     *Director of the United States Patent and Trademark Office*

UNITED STATES PATENT AND TRADEMARK OFFICE
CERTIFICATE OF CORRECTION

PATENT NO.     : 5,244,813
DATED          : September 14, 1993
INVENTOR(S)    : David R. Walt and Steven M. Bernard It is certified that error appears in the above-identified patent and that said Letters Patent is hereby corrected as shown below:

<u>Column 1,</u>
Line 5, after title "FIBER OPTIC SENSOR, APPARATUS, AND METHODS FOR DETECTING AN ORGANIC ANALYTE IN A FLUID OR VAPOR SAMPLE, insert the following paragraph:

-- This invention was made with government support under CR82030102 awarded by the Environmental Protection Agency. The government has certain rights in the invention. --

This certificate supersedes Certificate of Correction issued June 4, 2002.

Signed and Sealed this

Fifteenth Day of October, 2002

*Attest:*

*Attesting Officer*

JAMES E. ROGAN
*Director of the United States Patent and Trademark Office*